United States Patent [19]

Hauck et al.

[11] 3,984,407
[45] Oct. 5, 1976

[54] DIENE INTERMEDIATES FOR INDANTETROL DERIVATIVES

[75] Inventors: Frederic Peter Hauck, Somerville; Joyce Reid, Highland Park; Venkatachala L. Narayanan, Hightstown; Christopher M. Cimarusti, Hamilton; Rudiger D. Haugwitz, Titusville, all of N.J.; Joseph E. Sundeen, Yardley, Pa.

[73] Assignee: E. R. Squibb & Sons, Inc., Princeton, N.J.

[22] Filed: Apr. 21, 1975

[21] Appl. No.: 570,121

Related U.S. Application Data

[60] Division of Ser. No. 372,448, June 21, 1973, Pat. No. 3,894,031, which is a continuation of Ser. No. 71,229, Sept. 10, 1970, abandoned.

[52] U.S. Cl. .................... 260/247; 260/239 BC; 260/243 B; 260/247.5 R; 260/268 BC; 260/293.56; 260/326.8; 260/326.85; 260/463; 260/556 N; 260/558 R; 260/561 R; 260/563 P; 260/563 C; 260/570.8 R; 260/570.9; 260/577; 424/244; 424/246; 424/248; 424/250; 424/267; 424/274; 424/300; 424/301; 424/311; 424/325

[51] Int. Cl.² ....................... C07D 295/02

[58] Field of Search ............... 260/247.2 B, 268 BC, 260/293.56, 326.33, 326.5 R, 482 C, 488 B, 563 P, 239 BC, 243 B, 561 R, 563 C, 556 N, 558 R, 570.8, 570.9 R, 577, 247, 247.5 R, 326.8, 336.85

[56] References Cited

OTHER PUBLICATIONS
Cohen et al., Chem. Abstracts, (3)52:7311g (1958).

*Primary Examiner*—G. Thomas Todd
*Attorney, Agent, or Firm*—Lawrence S. Levinson; Merle J. Smith; Burton Rodney

[57] ABSTRACT

Compounds are provided having the structure

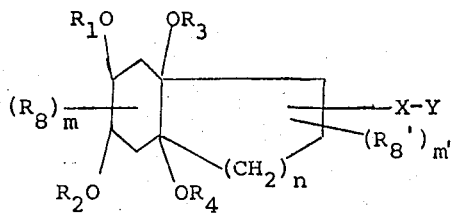

wherein $n$ is 1, 2 or 3, $m$ and $m'$ are 0, 1 or 2, $R_1$, $R_2$, $R_3$ and $R_4$ may be the same or different and can be hydrogen, lower alkyl, halolower alkyl, acyl, lower alkoxy-carbonyl amido 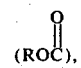

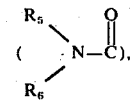

or lower alkoxyalkylene, X is a straight or branched bivalent aliphatic radical and Y is

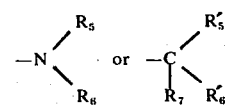

These compounds are useful in the treatment of hypertension.

15 Claims, No Drawings

DIENE INTERMEDIATES FOR INDANTETROL DERIVATIVES

RELATED APPLICATIONS

This application is a division of application Ser. No. 372,448 filed June 21, 1973, now U.S. Pat. No. 3,894,031, which in turn is a continuation of copending application Ser. No. 71,229 filed Sept. 10, 1970, now abandoned by Frederic P. Hauck et al., and entitled Indantetrol Derivatives.

COMPOUNDS OF THE INVENTION

The present invention relates to indanyl, naphthyl and benzosuberanyl derivatives which have a lowering effect on blood pressure and are useful in the treatment of hypertension, in mammalian species, for example, rats and dogs. In addition, the compounds of the invention can be employed as antibiotics. A compound of formula I (below) as well as its physiologically acceptable acid salts may be compounded according to pharmaceutical practice in oral or parenteral dosage forms such as tablets, capsules, elixirs, injectables or powders for administration of about 100 mg. to 400 mg. per day, preferably 125 mg. to 175 mg. per day, in 2 to 4 divided doses.

Furthermore, the compounds of this invention are useful as water softeners.

The compounds of the invention have the general formula:

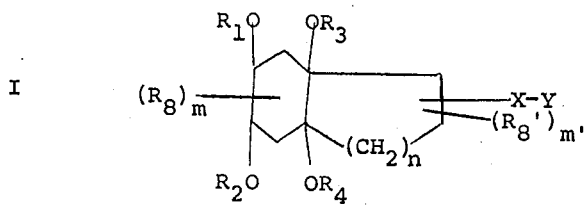

I wherein $n$ is 1, 2 or 3, $m$ and $m'$ are 0, 1 or 2, $R_1$, $R_2$, $R_3$ and $R_4$ may be the same or different and represent hydrogen, acyl, lower alkyl, halo-lower alkyl, lower alkoxy carbonyl

(ROC), amido

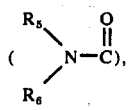

or lower alkoxyalkylene, $R_8$ and $R_8'$ are lower alkyl or monocyclic cycloalkyl, X is a single bond or a straight or branched chain bivalent aliphatic radical, and Y is

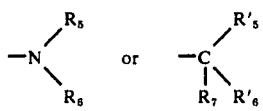

$R_7$ represent hydrogen or a lower alkyl, arylalkyl, or lower alkoxy; $R_5$ and $R_6$ may be the same or different, representing hydrogen, lower alkyl, lower alkoxyalkyl, halo-lower alkyl, monocyclic cycloalkyl, monocyclic cycloalkyl-lower alkyl, lower alkanoyl, halo-lower alkanoyl, hydroxy-lower alkyl, monocyclic aryloyl, monocyclic aryl, monocyclic aryl-lower alkyl, monocyclic heterocyclic, monocyclic heterocyclic alkyl or N,-N-dialkyl sulfamoyl; $R'_5$ and $R'_6$ can be any of the $R_5$ and $R_6$ radicals as well as a heterocycle such as pyridine, quinoline, or isoquinoline; at least one of $R'_5$, $R'_6$ and-/or $R_7$ includes a nitrogen atom. The

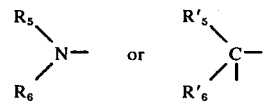

group may also form a heterocyclic radical.

X represents straight or branched chain bivalent aliphatic hydrocarbon groups having from zero to about 10 carbon atoms, such as an alkylene group of the structure $(CH_2)_{n'}$, wherein $n'$ is zero to 10, such as methylene, ethylene, propylene, trimethylene, butylene, dimethylethylene, and the like. Furthermore, X can correspond to any of the lower alkyl groups exemplified hereinafter; $R_1$, $R_2$, $R_3$ and/or $R_4$ and $R_5$ and/or $R_6$ may be an acyl radical of a hydrocarbon carboxylic acid of less than twelve carbon atoms, which may be exemplified by the lower alkanoic acids (e.g., formic, acetic, propionic, butyric, valeric, trimethyl acetic and caproic acids), the lower alkenoic acids (e.g., acrylic, methacrylic, crotonic, 3-butenoic and senecioic acids), the monocyclic aryl-carboxylic acids (e.g., benzoic and toluic acids), the monocyclic aryllower alkanoic acids [e.g., phenacetic, β-phenylpropionic, α-phenylbutyric, and 5-(p-methylphenyl)pentanoic acids], the cycloalkyl carboxylic acids (e.g., cyclobutane carboxylic acid, cyclopentane carboxylic acid and cyclohexane carboxylic acid), the cycloalkenyl carboxylic acids (e.g., 2-cyclobutene carboxylic acid and 3-cyclopentene carboxylic acid), the cycloalkyl and cycloalkenyl-lower alkanoic acids [e.g., cyclohexaneacetic, α-cyclopentanebutyric, 2-cyclopenteneacetic and 3-(3-cyclohexene) pentenoic acid], and the like.

The alkanoic acids may include halogen substituents, for example, trifluoroacetic acid. In addition, other acyl groups which can be employed are angeloyl, veratroyl, vanilloyl, erythro-2-hydroxy-2-methyl-3-acetoxybutyryl, (1)-2-methylbutyryl; (d)-2-hydroxy-2-methylbutyryl; (d)-threo-2,3-dihydroxy-2-methylbutyryl and (1)-erythro-2,3-dihydroxy-2-methylbutyryl.

The term "lower alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Alkyl radicals substituted by F, Br, Cl or I are encompassed by the term halo-lower alkyl. Trifluoromethyl is a preferred halo-lower alkyl radical.

The term "lower alkoxy" includes straight and branched chain radicals which correspond to the above lower alkyl groups attached to an oxygen atom.

The term "monocyclic aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like). di(lower alkyl)phenyl (e.g., 2,4-dimethylphenyl, 3,5-diethylphenyl, and the like), halophenyl (e.g., chlorophenyl, bromophenyl, iodophenyl, fluorophenyl), o-, m- or p-nitrophenyl, dinitrophenyl, (e.g., 3,5-dinitrophenyl, 2,6-dinitrophenyl, and the like), trinitrophenyl (e.g., picryl).

The term "monocyclic aryoyl" includes any of the above aryl groups linked to a carbonyl group.

The term "monocyclic cycloalkyl" and "monocyclic cycloalkenyl" includes cyclic radicals containing from 3 to 6 ring members (e.g., cyclopropyl, cyclobutyl, cyclopentyl, cyclohexyl, cyclobutenyl and cyclohexenyl).

As indicated hereinbefore

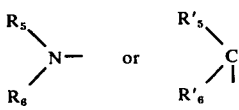

may form a heterocyclic radical. The symbols $R_5$ and $R_6$ and $R'_5$ and $R'_6$ may together represent the carbon (and hydrogen) and the oxygen, sulfur or nitrogen atoms which, with the nitrogen or carbon atoms in the above group, form a 5-, 6- or 7-membered nitrogen heterocyclic containing not more than one hetero atom in addition to the nitrogen already shown in the group and less than 21 atoms in the radical (excluding hydrogen). The heterocyclic radicals may include one to three substituents including lower alkoxy or lower alkyl as defined hereinafter; trihalomethoxy, such as trifluoromethoxy; trihalomethylmercapto, such as trifluoromethylmercapto; N,N,-dialkylsulfamoyl groups, such as N,N-dimethylsulfamoyl; lower alkanoyl groups as defined hereinafter such as acetyl, propionyl, and the like; hydroxy; hydroxy-lower alkyl, such as hydroxymethyl, 2-hydroxyethyl, or the like; hydroxy-lower alkoxy-lower alkyl, such as 2-(2-hydroxyethoxy)ethyl, or the like; alkanoyloxy containing an alkanoyl as defined herein; alkanoyloxy-lower alkyl (up to about 14 carbons in the alkanoyl group), such as 2-heptanoyloxyethyl; carbo-lower alkoxy, such as carbomethoxy, carboethoxy, carbopropoxy, or the like; or 2-(alkanoyloxy-lower alkoxy) lower alkyl (with up to about 14 carbons in the alkanoyl group), such as 2-(decanoyloxyethoxy)-ethyl, or the like.

Illustrative of the heterocyclic radicals represented by $R_5$, $R_6$,

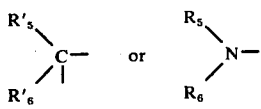

are the following: piperidino; (lower alkyl)piperidino [e.g., 2-, 3-, or 4-(lower alkyl)piperidino or 4-(N-lower alkyl)piperidino such as 2-(ethyl)piperidino or 4-(N-isopropyl)-piperidino]; di(lower alkyl)piperidino [e.g., 2,4-, 2,5- or 3,5-di(lower alkyl)piperidino such as 2,4-dimethylpiperidino or 2,5-di-t-butyl piperidino]; (lower alkoxy)piperidino [e.g., 2-methoxypiperidino or 3-methoxypiperidino]; hydroxypiperidino [e.g., 3-hydroxy- or 4-hydroxypiperidino]; aminomethylpiperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4dimethylpyrrolidino]; (lower alkoxy)pyrrolidino [e.g., 2-methoxypyrrolidino]; morpholino; (lower alkyl)morpholine [e.g., 3-methylmorpholino]; di(lower alkyl)morpholino [e.g., 3,5-dimethylmorpholino]; (lower alkoxy)morpholino [e.g. 2-methoxymorpholino]; thiamorpholino; (lower alkyl)thiamorpholino [e.g., 3-methylthiamorpholino]; di(lower alkyl)thiamorpholino [e.g., 3,5-dimethylthiamorpholino; (lower alkoxy)-thiamorpholino [e.g., 3-methoxythiamorpholino]; piperazino; (lower alkyl)piperazino [e.g., $N^4$-methylpiperazino]; di(lower alkyl)piperazino [e.g., 2,5-dimethylpiperazino or 2,6-dimethylpiperazino]; (lower alkoxy)piperazino [e.g., 2-methoxypiperazino]; (hydroxy-lower alkyl)piperazino [e.g., $N^4$-(2-hydroxyethyl)piperazino]; (alkanoyloxy-lower alkyl)piperazino wherein the alkanoyloxy group has up to 14 carbons [e.g., $N^4$-(2-heptanoyloxyethyl)piperazino or $N^4$-(2-dodecanoyloxyethyl)piperazino]; (hydroxy-lower alkoxy-lower alkyl)piperazino [e.g., (hydroxy-methoxymethyl)piperazino]; (carbo-lower alkoxy)piperazino [e.g., $N^4$-(carbomethoxy-, carboethoxy-, or carbopropoxy)piperazino]; homopiperazino; or $N^4$-(hydroxylower alkyl)homopiperazino [e.g., $N^4$-(2-hydroxyethyl)homopiperazino]; piperidyl; (lower alkyl)piperidyl [e.g., 1-, 2-, 3- or 4-(lower alkyl)piperidyl, such as 1-N-methylpiperidyl or 3-ethylpiperidyl]; di(-lower alkyl)piperidyl [e.g., 2,4-, 2,5-, or 3,5-di(lower alkyl)piperidyl wherein lower alkyl is methyl, ethyl, n-propyl, isopropyl, etc.]; lower alkoxy piperidyl [e.g., 3-methoxypiperidyl or 2-ethoxypiperidyl]; hydroxy piperidyl [e.g., 3-hydroxy- or 4-hydroxypiperidyl]; aminomethylpiperidyl [e.g., 4-aminoethylpiperidyl]; pyrrolidyl; lower alkyl pyrrolidyl [e.g., 1-N-methylpyrrolidyl]; di(lower alkyl)pyrrolidyl [e.g., 2,3-dimethylpyrrolidyl]; lower alkoxy pyrrolidyl [e.g., 4-N-methoxypyrrolidyl]; morpholinyl; (lower alkyl)morpholinyl [e.g., 3-methylmorpholinyl]; di(lower alkyl)morpholinyl [e.g., 3-methyl-4-N-ethylmorpholinyl]; (lower alkoxy)morpholinyl [e.g., 2-ethoxymorpholinyl]; thiamorpholinyl; (lower alkyl)thiamorpholinyl [e.g., 3-ethylthiamorpholinyl]; di(lower alkyl)thiamorpholinyl [e.g., 3-methyl-4-N-ethylthiamorpholinyl]; lower alkoxy thiamorpholino [e.g., 3-methoxythiamorpholinyl]; piperazinyl; alkyl, dialkyl, alkoxy or hydroxy-lower alkyl substituted piperazinyl.

The N-oxides of the compounds of formula I where Y represents a nitrogen containing heterocyclic radical can be formed by reacting such formula I compounds with a peracid such as m-chloroperoxy benzoic acid, perbenzoic acid or monoperphthalic acid in a suitable solvent such as chloroform.

The compounds of formula I form acid addition salts by reaction with various inorganic acids. These salts frequently provide convenient means for separating the product from the reaction mixture in which it is produced or from the solvent in which it is extracted in view of their insolubility in various media. Thus the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acid salts such as phosphate, sulfate, nitrate, etc., organic acid salts such as oxalate, tartrate, malate, maleate, citrate, pamoate, 5,6,7 camphorsulfonate, methanesulfonate, benzenesulfonate, toluenesulfonate, salicylate, benzoate, ascorbate, mandelate, or the like.

The compounds of formula I also form quaternary ammonium salts with lower alkyl halides, for example, methyl bromide, ethyl bromide and propyl iodide; benzyl halides, such as benzyl chloride; and dilower alkyl sulfates, such as dimethyl sulfate. To form the quaternary ammonium salts, the free base initially formed is interreacted with at least one equivalent of the desired alkylating agent.

Formula I includes all stereoisomers and mixtures thereof. Thus, Formula I includes compounds of the structure:

(A) 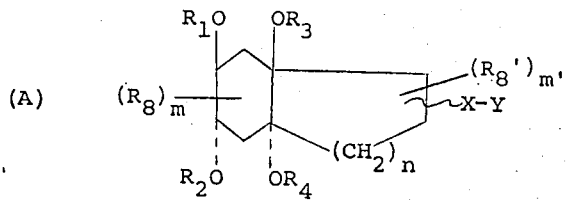

wherein all four OR groups are axial and $R_1O$ and $R_2O$ are in trans configuration and $OR_3$ and $OR_4$ are in trans configuration.

(C) 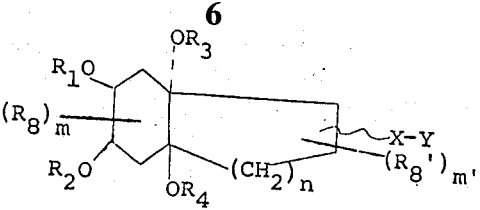

wherein $R_1O$ and $R_2O$ are in cis configuration and $OR_3$ and $OR_4$ are in trans configuration and one of $R_1O$ and $R_2O$ is equatorial and the other axial and $OR_3$ and $OR_4$ are diaxial.

(D) 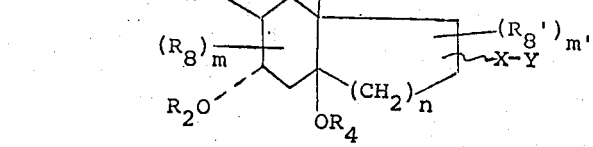

wherein $R_1O$ and $R_2O$ are in trans configuration and $OR_3$ and $OR_4$ are in cis configuration and $R_1O$ and $R_2O$ are diequatorial or diaxial and one of $OR_3$ and $OR_4$ is equatorial and the other axial.

(E)

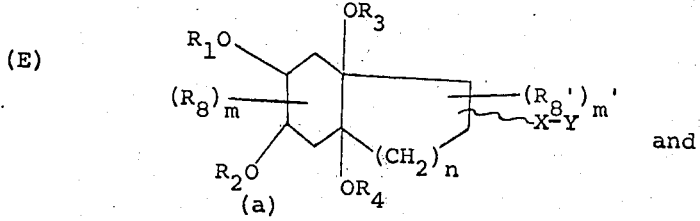
(a)

and

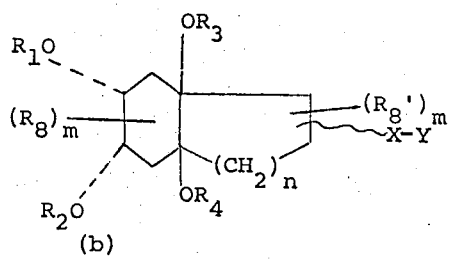
(b)

(B) 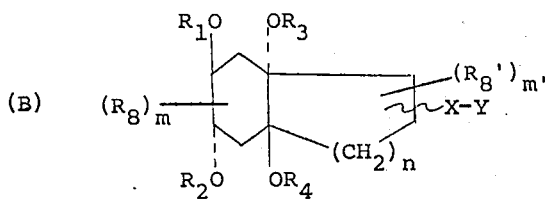

wherein $R_1O$ and $R_2O$ are in trans configuration, and $OR_3$ and $OR_4$ are in trans configuration and $R_3O$ and $R_4O$ are diaxial and $R_1O$ and $R_2O$ are diequatorial.

wherein in (a) $R_1O$ and $R_2O$ are in cis configuration and $OR_3$ and $OR_4$ are in cis configuration and the pair of $R_1O$ and $R_2O$ and the pair of $OR_3$ and $OR_4$ are in cis configuration and wherein in (b) $R_1O$ and $R_2O$ are in cis configuration and $OR_3$ and $OR_4$ are in cis configuration and the pair of $R_1O$ and $R_2O$ and the pair of $OR_3$ and $OR_4$ are in trans configuration.

In each of (A) through (E)—X—Y can be up or down.

Preferred compounds are those where $n$ is 1, X is $(CH_2)_3$, Y is an amino group, $R_1$, $R_2$, $R_3$ and $R_4$ are acyl, $m$ and $m'$ are 0, but where $m$ is 1 or 2, the $R_8$ group is preferably at the 5 and/or 6 positions.

Examples of tetrols and esters thereof falling within the present invention are as follows:
1. 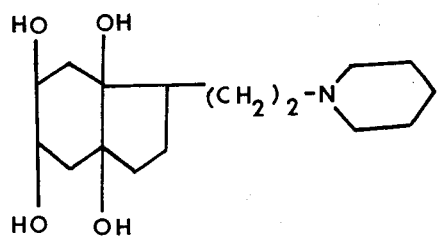
2. 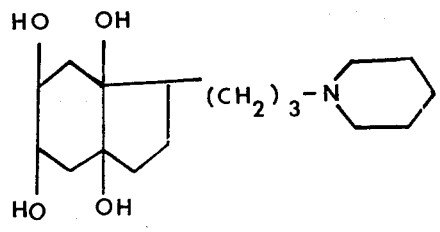
3. 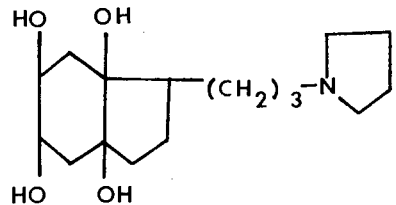
4. 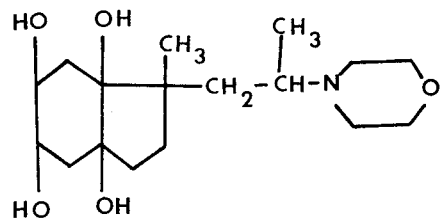
5. 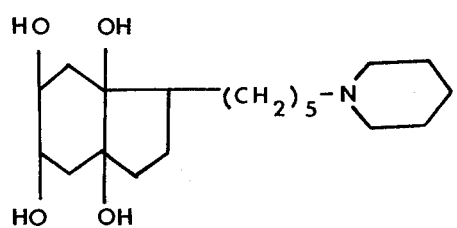
6. 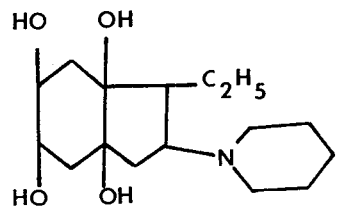
7. 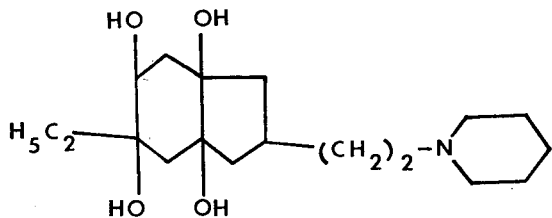

8. 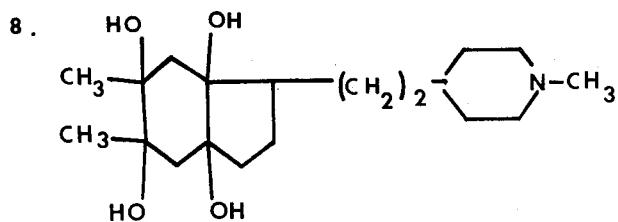
9. 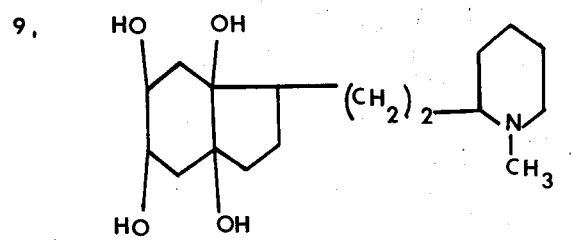
10. 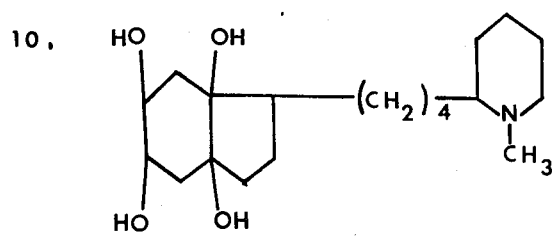
11. 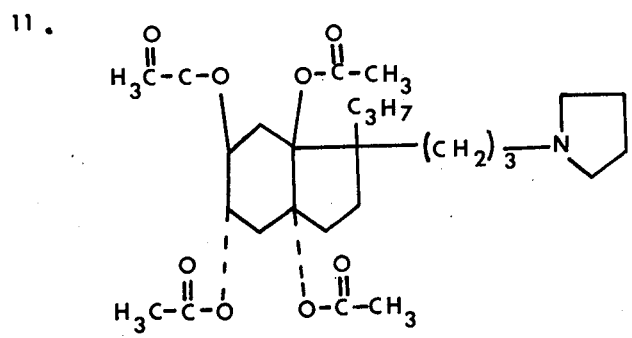
12. 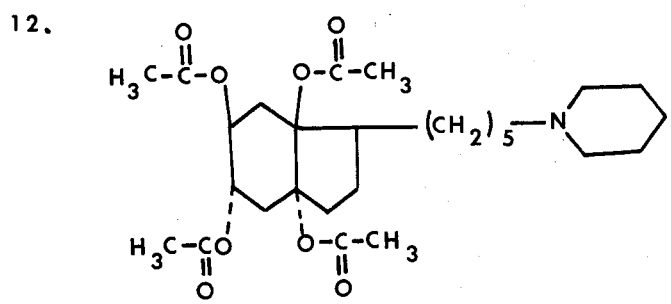
13. 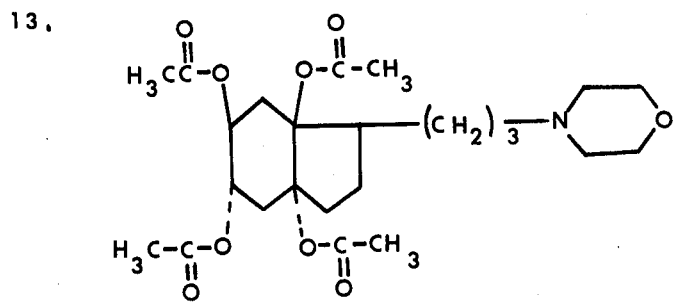

14. 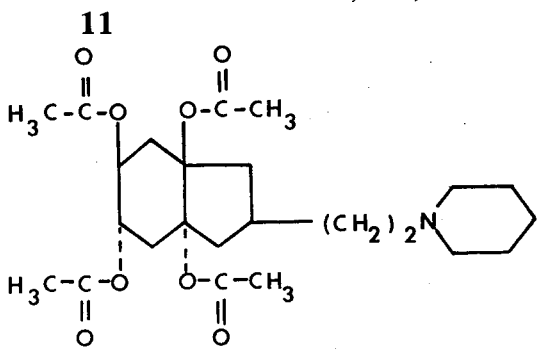
15. 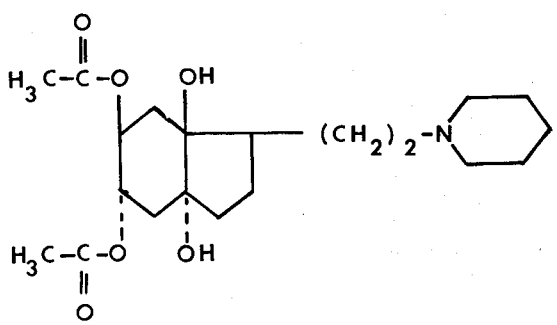
16. 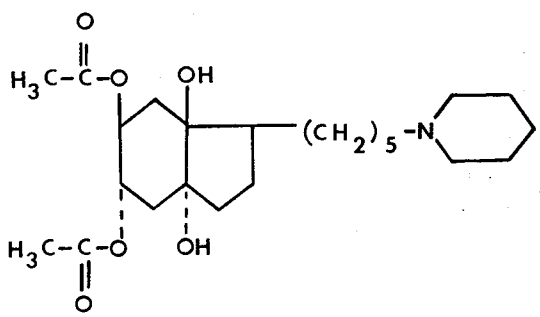
17. 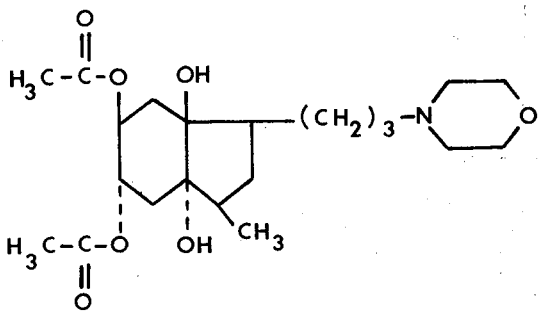
18. 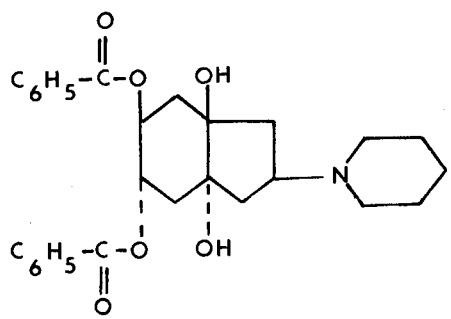

19 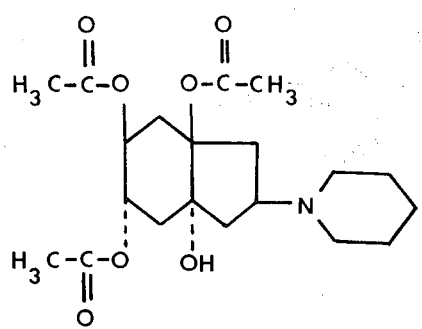
20 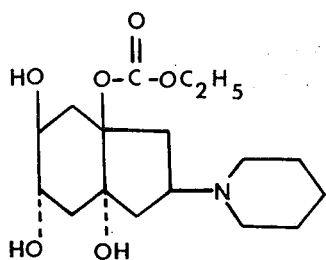
21 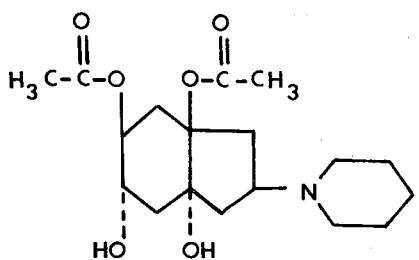
22 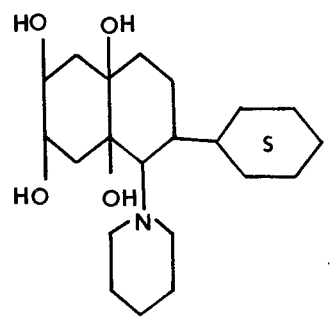
23 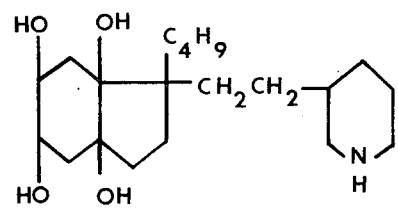
24. 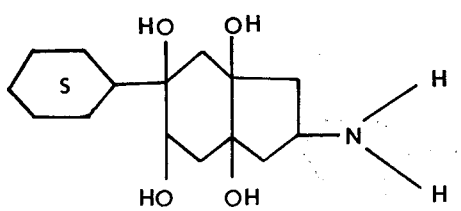
25. 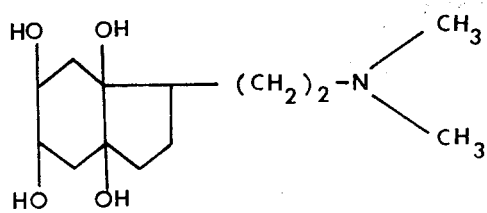

26. 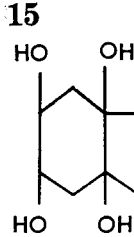 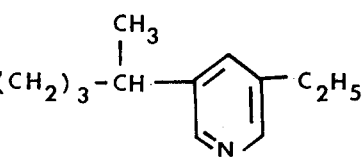
27. 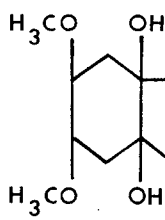 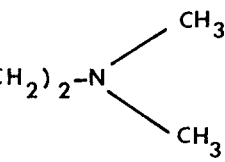
28. 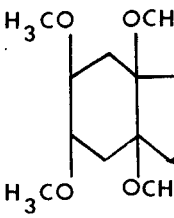 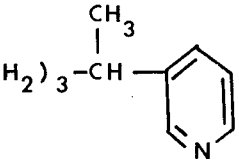
29. 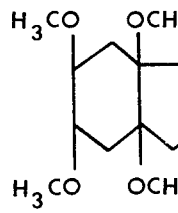 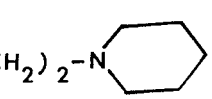
30. 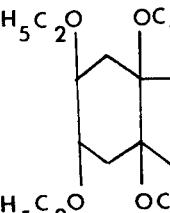 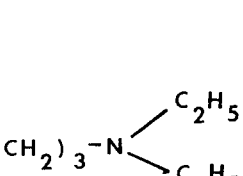
31. 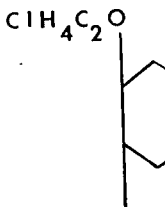 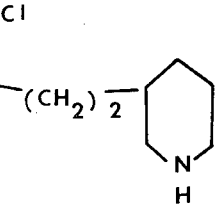
32. 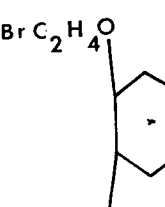 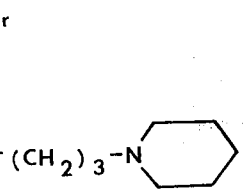

33. 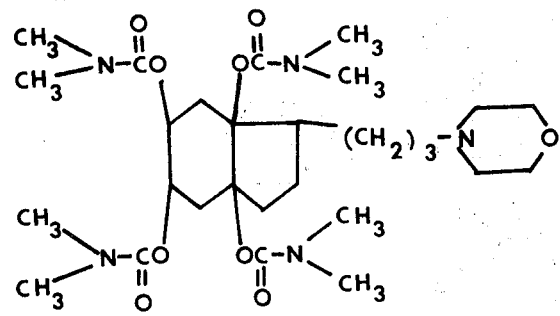
34 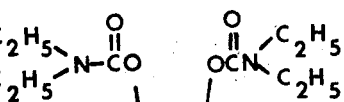
35. 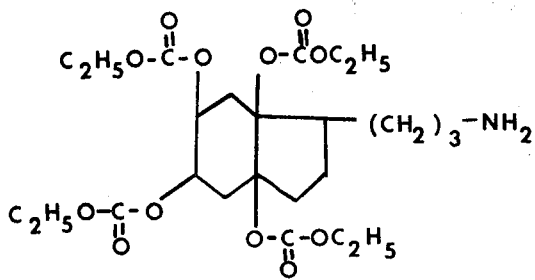
36. 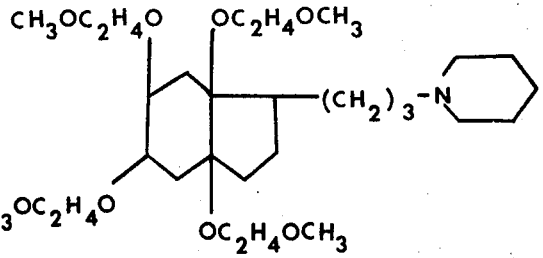
37. 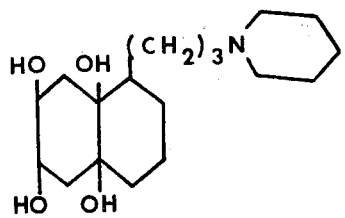
38. 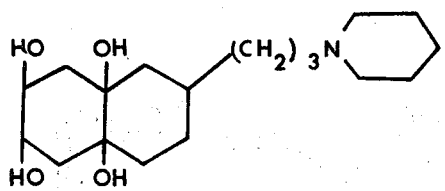
39. 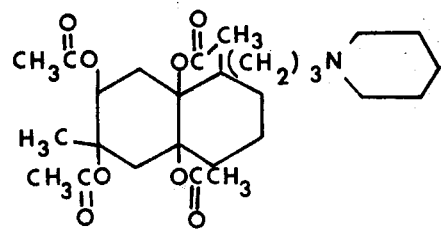

40. 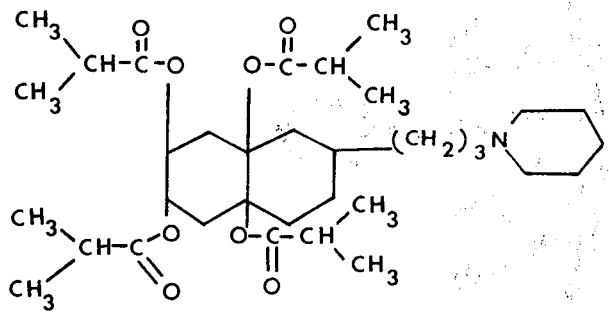
41. 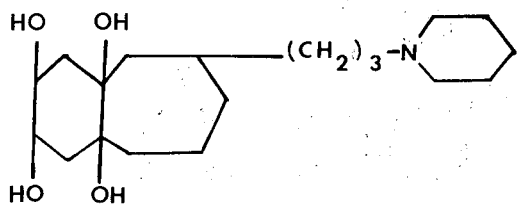
42. 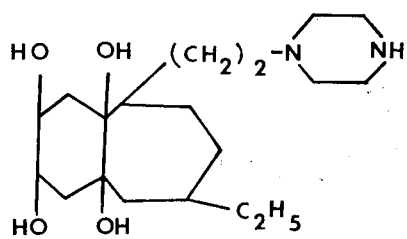
43. 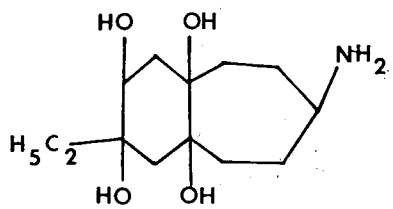
44. 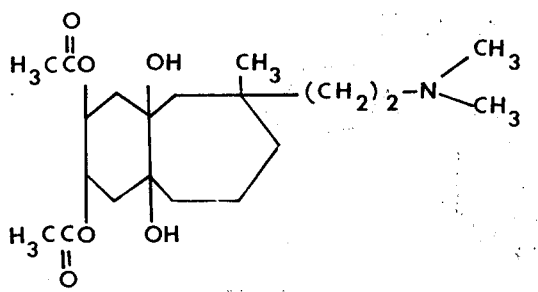
45. 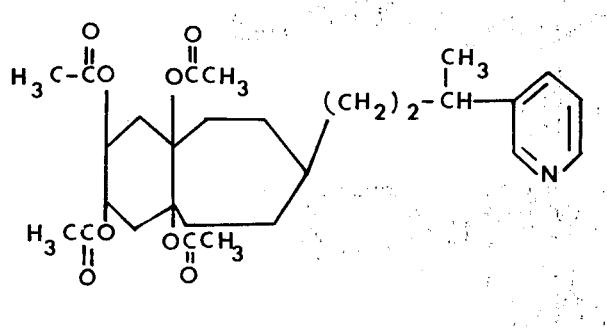

Each of the above structures represent each of the possible isomers as outlined hereinbefore as well as mixtures of such isomers.

METHODS OF PREPARATION

Further, in accordance with the present invention, a process is provided for preparing the compounds of Formula I of the invention wherein the $OR_1$, $OR_2$, $OR_3$, and $OR_4$ are all axial (Type A), which comprises forming a diene of the structure II
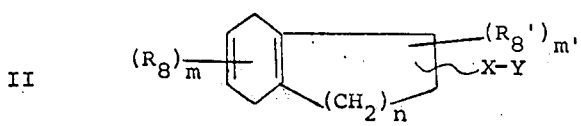

and converting the diene to the tetrol or tetrol derivatives of Formula I.

The tetrol (Type A) wherein $R_1$, $R_2$, $R_3$ and $R_4$ are hydrogen, can be formed by hydroxylating the diene to the corresponding tetrol, for example, by reacting the diene with formic acid and aqueous hydrogen peroxide, at temperatures ranging from about 20° to about 40°C. to form a mixture of esters, and then subjecting the mixture of esters to basic hydrolysis by dissolving the mixture of esters in a solvent boiling below about 100°C., such as a monohydric alcohol containing up to four carbon atoms (e.g., methyl alcohol, ethyl alcohol, propyl alcohol, isopropyl alcohol or butyl alcohol), and then treating the solution with a base, such as an alkali metal or alkaline earth metal hydroxide or alkoxide (e.g., sodium hydroxide, potassium hydroxide, barium hydroxide, calcium hydroxide, sodium methoxide or calcium diethoxide) and heating the mixture to temperatures ranging from about 40° to about 80°C., to form a tetrol (Type A) of the structure:

III
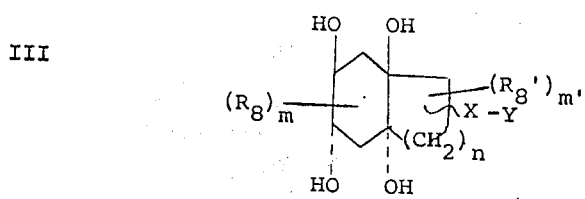

wherein all hydroxyl groups are axial.

In the above reaction the hydrogen peroxide is employed in a molar ratio to the diene of within the range of from about 2.2:1 to about 15:1 and preferably from about 2.2:1 to about 5:1. The base is employed in a molar ratio to the mixture of esters of within the range of from about 2.2:1 to about 10:1 and preferably from about 2.2:1 to about 5:1.

The Type(A)tetrol of Formula III can be converted to the corresponding tetra ester, i.e., where $R_1$, $R_2$, $R_3$ and $R_4$ are acyl as defined hereinbefore, by reacting the tetrol with an acylating agent, such as a hydrocarbon carboxylic acid containing less than twelve carbon atoms as discussed hereinbefore, the acid anhydride thereof, or corresponding acyl halide, and an acid catalyst, such as perchloric acid, at a temperature within the range of from about −20° to about 0°C. The acid, acid anhydride or acyl halide is employed in a molar ratio to the tetrol of within the range of from about 4:1 to about 20:1 and preferably from about 4:1 to about 10:1 and the acid catalyst is employed in a molar ratio to the tetrol of within the rage of from about 1.1:1 to about 2:1 and preferably from about 1.1:1 to about 1.5:1.

The tetrol of Formula III can be converted to the corresponding diester wherein $R_1$ and $R_2$ are acyl and $R_3$ and $R_4$ are hydrogen, by dissolving the tetrol in a organic base, such as pyridine, and treating the solution with an acylating agent such as an acid anhydride (as described hereinbefore) or corresponding acyl halide in a molar ratio of acylating agent-tetrol of within the range of from about 2.1:1 to about 10:1 and preferably from about 2.2:1 to about 6:1, while maintaining the reaction mixture at a temperature within the range of from about 0° to about 20° and preferably from about 5° to about 15° to form a diester of the structure

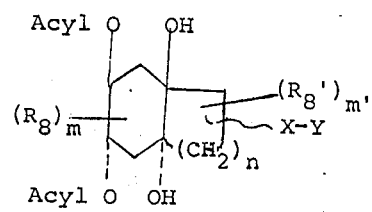

The type A tetrol III can be converted to the corresponding triester wherein $R_1$, $R_2$ and $R_3$ are acyl and $R_4$ is hydrogen and X is preferably a single bond, where the nitrogen atom of Y is suitably located to participate in the acylation, by mixing the tetrol with a base, preferably pyridine, and reacting the mixture with an acylating agent such as an acid anhydride or corresponding acyl halide (as defined herebefore) in a molar ratio of acylating agent-tetrol of within the range of from about 3:1 to about 10:1 and preferably from about 3:1 to about 5:1, at a temperature of within the range of from about 5° to about 40° and preferably from about 10° to about 30° to form a triester of the structure:

V
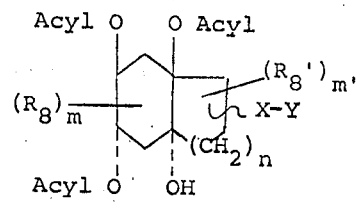

The above triester can be converted to the corresponding diester of the structure:

VI
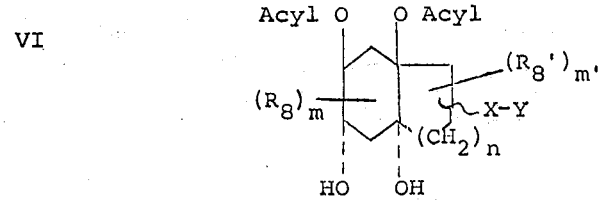

by treating the triester with an alcohol-water mixture in a volume ratio of alcohol:water within the range of from about 9:1 to about 1:1 and preferably from about 1:1 to about 3:1. The alcohol-water mixture is employed in a weight ratio to the triester of within the range of from about 10:1 to about 100:1 and preferably from about 10:1 to about 50:1.

The tetrol III can be converted to the corresponding monoester wherein $R_3$ is acyl and $R_1$, $R_2$ and $R_4$ are hydrogen by treating the tetrol with a haloalkyl carbonate in a molar ratio of carbonate-tetrol of within the range of from about 1.1:1 to about 100:1 and preferably from about 10:1 to about 50:1 at a temperature within the range of from about 20° to about 60° and preferably from about 25° to about 35° to form a monoester of the structure:

VII 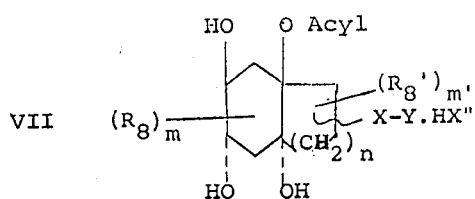

wherein X" is a halogen.

In an alternative procedure, the diene of formula II can be converted to the corresponding tetrol by dissolving the diene II in an organic carboxylic acid having up to about eight carbon atoms, such as acetic acid, treating the mixture with a silver salt corresponding to the acid, such as silver acetate (in a molar ratio of diene to silver salt of within the range of from about 1:2 to about 1:4 and preferably about 1:2) and iodine (in a molar ratio of diene to iodine of 1:1), heating the reaction mixture at a temperature of within the range of from about 60° to about 110° and preferably from about 80° to about 100°, to form a diester (depending on which acid and silver salt are employed) of the structure:

VIII 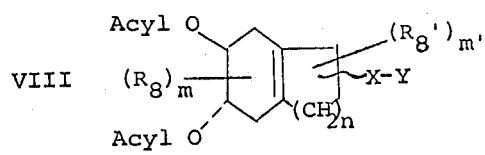

The above diester of the structure VIII can be converted to the corresponding tetrol of Type (A) by dissolving the diester in a suitable protonic solvent, such as ethyl alcohol, treating the solution with an excess of an aqueous base, such as aqueous sodium hydroxide or potassium hydroxide, to effect hydrolysis to the corresponding diol of the structure:

IX 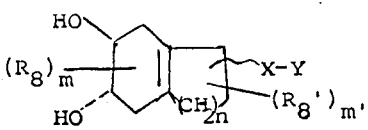

The above diol can be converted to the tetrol by reacting the formic acid and hydrogen peroxide (as described hereinbefore), at temperatures ranging from about 20° to about 40°C., preferably about 35°, and then treating the mixture (free of solvent) with an alcohol and a base (as described hereinbefore) to form the tetrol wherein all OR's are axial and each pair of OR's are trans. (Type (A)).

The tetrol isomer or derivatives thereof of Type (A) can also be prepared by reacting the diene II with formic acid and one equivalent of an oxidizing agent, such as aqueous hydrogen peroxide, and after removal of solvent, dissolving the residue in an alcohol-base as described hereinbefore to effect hydrolysis and form a diol olefin of the structure:

X 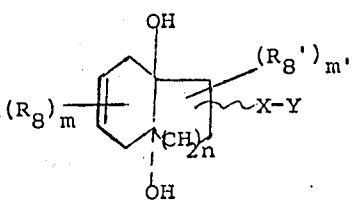

The above diol olefin can then be converted to the tetrol of type (A) as described hereinbefore with respect to the conversion of the diol olefin IX.

Where Y is

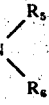

and at least one of $R_5$ and $R_6$ is or includes a aromatic ring, the Type (A) tetrols of the invention can be prepared by reducing a hydroxyalkyl compound of the structue:

XI 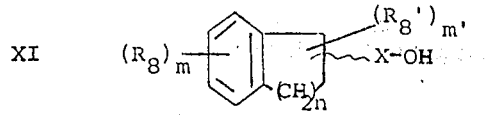

wherein X is lower alkylene as defined hereinbefore with respect to the corresponding diene, by reacting the indene with a reducing metal, such as lithium or sodium in liquid ammonia in the presence of a proton source such as a lower alcohol, to form the corresponding hydroxyalkyl diene of the structure:

XII 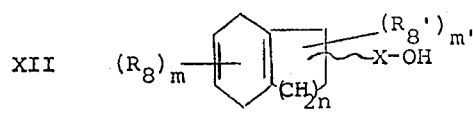

dissolving the hydroxyalkyl diene in a basic organic solvent, such as pyridine, cooling the solution to below 0°, treating the solution with a solution of p-toluene sulfonyl chloride in pyridine, in a molar ratio of diene to p-toluene sulfonyl chloride of within the range of from about 1:1 to about 1:1.5, and cooling to form the corresponding diene tosylate of the structure:

XIII
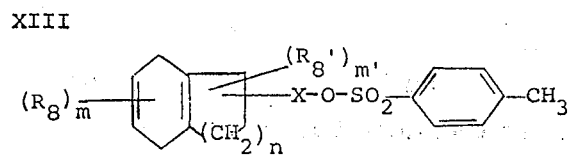

reacting the diene tosylate with an arylamine or substituted arylamine, aryl lower alkylamine or substituted aryl lower alkylamine or an amine of the structure

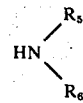

(in a molar ratio of tosylate to amine of within the range of from about 1:2 to about 1:5) in a aromatic solvent boiling below about 120°C., such as toluene or benzene to form an aminoalkyldiene of the structure:

XIV 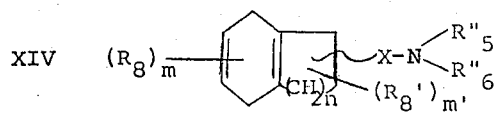

wherein $R''_5$ and $R''_6$ is the same or different and can be aryl, substituted aryl, arylalkyl, substituted arylalkyl or any of the $R_5$ and $R_6$ substituents mentioned previously. The substituted aryl groups can include any of the substituents set out hereinbefore with respect to the heterocyclic groups. The aminoalkyl diene can be converted to the corresponding tetrol by reacting the diene with formic acid and a oxidizing agent, such as hydrogen peroxide, removing solvent and subjecting the residue to basic hydrolysis (alcohol-base) as described hereinbefore, to form a tetrol of the structure:

XV 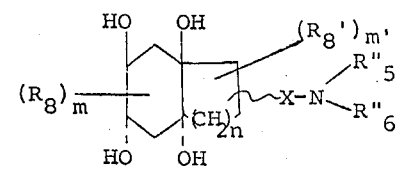

wherein $R'_5$ and $R'_6$ are as defined above. When $R''_5$ or $R''_6$ is benzyl it can be converted to a hydrogen atom by treating the tetrol with hydrogen in the presence of a catalyst for reduction, such as palladium on strontium carbonate.

Where Y is $NH_2$, the Type (A) tetrols of the invention can be prepared by reacting an aminoalkyl indene (prepared by reduction of the corresponding cyanoalkyl indene) or an aminoalkyl tetrahydronaphthalene with a reducing agent, such as lithium ribbon in the presence of liquid ammonia, ethyl ether, and a proton source such as a lower alcohol, to form a diene of the structure:

XVI 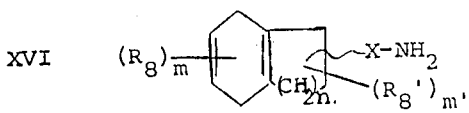

(B) 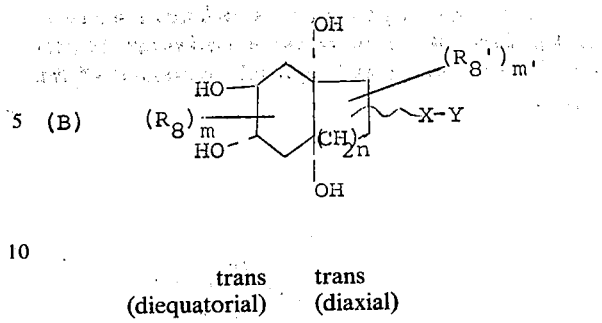

trans    trans
(diequatorial)  (diaxial)

and reacting the diene with an acyl halide (wherein acyl and the halogen are as defined hereinbefore), such as benzoyl chloride, in a molar ratio of diene: halide of within the range of from about 1:1 to about 2:1 in a basic solvent, such as pyridine, triethylamine, or dilute to form a diene of the structure:

can be prepared by treating a diester olefin of the structure:

XVII 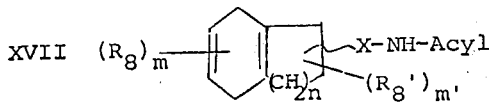

VIII 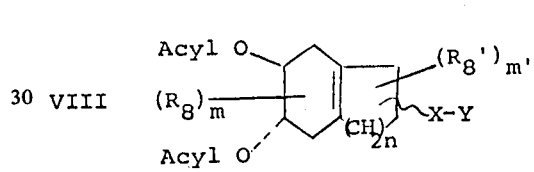

and reacting the diene with formic acid and an oxidizing agent, such as hydrogen peroxide, and subjecting the product to basic hydrolysis (as described hereinbefore) to form an aminoalkyl tetrol of the structure:

with formic acid and an oxidizing agent, such as hydrogen peroxide, at temperatures ranging from about 20° to about 40°C. and preferably from about 25° to about 35°C., and then treating the product with an alcohol-base, such as a monohydric alcohol and any of the bases mentioned hereinbefore and heating the mixture at temperatures ranging from about 40° to about 100° and preferably at reflux temperature to form a Type (B) tetrol.

Tetrol isomers of Type (C) or derivatives thereof having the formula:

XVIII 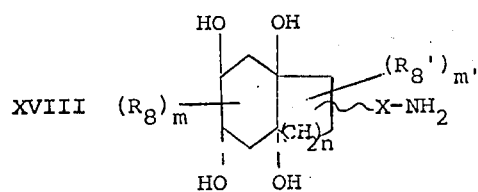

(C) 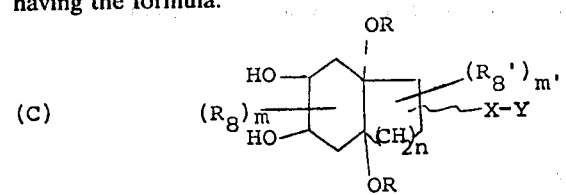

cis        trans
(equatorial-axial)  (diaxial)

Preparation of Other Isomers (Types B,C,D, and E)
Tetrol isomers of Type (B) or esters thereof, that is:

can be prepared by dissolving a diene of the structure:

II 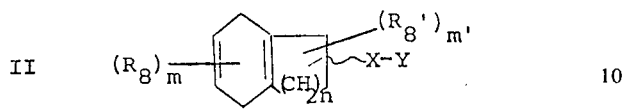

in an alkanoic acid containing from two to ten carbon atoms, such as acetic acid, containing from about 2 to about 10% water and preferably about 5% water, treating the solution with a silver salt corresponding to the acid, such as silver acetate and iodine in the same manner as described hereinbefore in the alternative procedure for preparing the Type (A) tetrol isomer, to form an olefin of the structure:

XIX 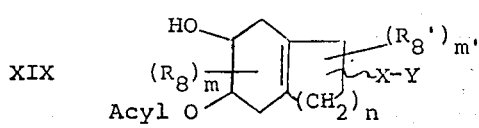

wherein X and Y are as defined hereinbefore (which is a novel intermediate).

The above monoalcohol monoester can be converted to the corresponding diol by basic hydrolysis, for example, by treatment with alcohol-base as described hereinbefore. The diol or the monoalcohol monoester can be converted to the Type (C) tetrol isomer by treating it with formic acid and an oxidizing agent, such as hydrogen peroxide and subsequently subjecting the resulting product to basic hydrolysis (all of which is described in detail hereinbefore in the preparation of the Type (A) isomer) to form the Type (C) tetrol isomer.

Tetrol isomers of Type (D) or esters thereof, that is:

(D) 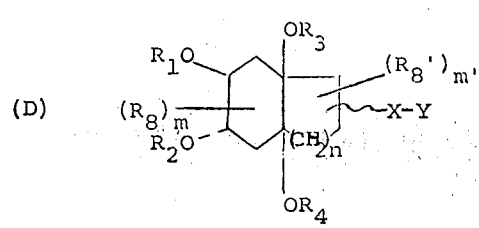

trans          cis (diequatorial or    (equatorial-axial)
diaxial)

can be prepared by converting a diene of the structure II to the corresponding diester olefin of the structure:

VIII 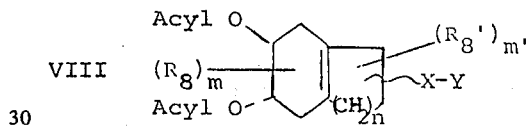

as described hereinbefore and then dissolving the diester olefin in a basic organic solvent, such as a mixture of pyridine and benzene, and treating the solution with osmium tetroxide in a molar ratio of $OsO_4$ to diester olefin of within the range from about 1:1 to about 4:1 and preferably about 1:1, to form a Type (D) diester diol isomer of the structure:

(D) 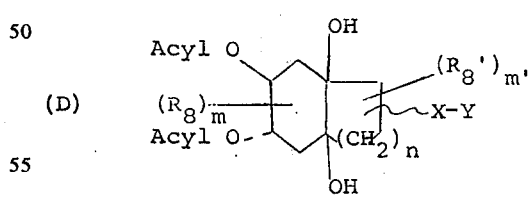

The type (D) diester diol isomer can be converted to the Type (D) tetrol isomer by basic hydrolysis as described hereinbefore with respect to the Type (A) isomer.

Tetrol isomers of Type (E) or esters thereof, that is

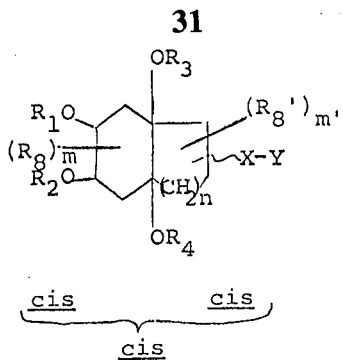

cis         cis
       cis and

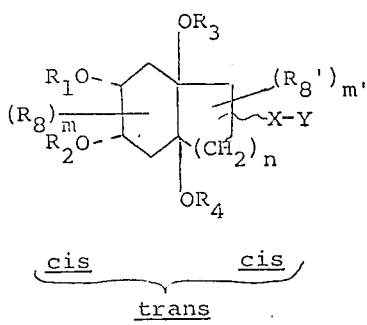

cis         cis
         trans can be prepared by converting a diene of the structure II to the corresponding monoalcohol monoester of the structure XIX as described hereinbefore in the preparation of the Type (C) isomer, dissolving the monoalcohol monoester in a basic solvent, for example, pyridine, treating the solution with an acid anhydride of an alkanoic acid containing up to about 6 carbon atoms, such as acetic anhydride or acid anhydrides of any of the alkanoic acids mentioned hereinbefore, in a molar ratio of monoalcohol monoester to acid anhydride of within the range of from about 1:1 to about 1:5 and preferably from about 1:1 to about 1:2, to form a diester olefin of the structure:

VIII 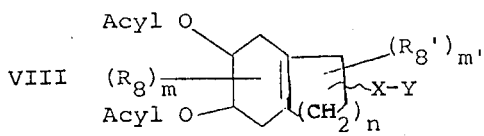

and then treating the diester olefin with pyridine and osmium tetroxide (as described hereinbefore in the preparation of the Type (D) isomer), to form a mixture of Type E diester diols of the structues:

(E) 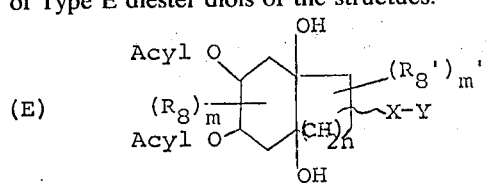

and

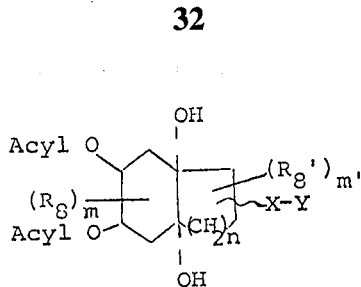

The diester diols can be converted to the corresponding Type (E) tetrols by basic hydrolysis as described hereinbefore in the preparation of the Type (A) isomers.

Preparation of Other Tetrol Derivatives

The tetrol ethers of formula I wherein $R_1$, $R_2$, $R_3$ and $R_4$ are lower alkyl can be prepared by dissolving a tetrol of Formula I in a suitable nonprotonic solvent such as benzene, dioxane, ethyl ether or tetrahydrofuran, adding to the solution at least four equivalents and preferably from about five to about seven equivalents of a metal hydride such as sodium hydride or sodium amide, thereafter adding to the mixture slowly with stirring about four equivalents of a lower alkyl halide such as methyl iodide, methyl bromide or ethyl iodide, and maintaining the temperature of the reaction mixture within the range of from about 20° to about 60°C. and preferably from about 30 to about 40°C., to form the tetrol ether. Thereafter, ethyl alcohol and/or water can be added to decompose excess base, and the tetrol ether can be recovered by stripping down the organic solvent.

Tetrols of Formula I wherein $R_1$, $R_2$, $R_3$ and $R_4$ are halo-lower alkyl can be formed as described hereinbefore with respect to the preparation of the tetrol ethers with the exception that a alkylene halohalide (or dihaloalkane) such as trimethylene chlorobromide or pentamethylene fluoro iodide, is employed in place of the alkyl halide.

Tetrols of Formula I wherein $R_1$, $R_2$, $R_3$ and $R_4$ are lower alkoxy carbonyl can be formed as described hereinbefore with respect to the preparation of the tetrol ethers with the exception that a dialkyl carbamoyl halide, such as dimethyl carbamoyl chloride or diethyl carbamoyl bromide, or a substituted isocyanate such as an alkyl or aryl isocyanate is employed in place of the alkyl halide.

Tetrols of Formula I wherein $R_1$, $R_2$, $R_3$ and $R_4$ are lower alkoxyalkylene wherein the alkylene group contains two to five carbon atoms can be formed as described hereinbefore with respect to the preparation of the tetrol ethers except that an alkoxyalkylene halide such as ethoxypropyl chloride or ethoxyethyl bromide is employed in place of the alkyl halide.

Tetrols of Formula I wherein $R_1$, $R_2$, $R_3$ and $R_4$ are $$R-O-\overset{\overset{O}{\|}}{C}-$$

can be formed as described hereinbefore with respect to the preparation of the tetrol ethers except than an alkylhaloformate such as methylchloroformate or ethylchloroformate is employed in place of the alkyl halide.

Alternative Methods for Preparing Naphthyl and Benzosuberanyl Derivatives 1,2,3,4,5,8-hexahydronaphthalenes of structures XX A and XX B

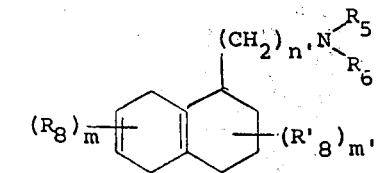

XX A

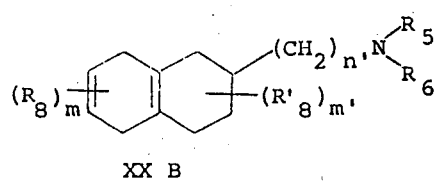

XX B may be prepared from tetralones in several ways know to the art. Reaction of α-tetralone with an aminoalkyl Grignard reagent followed by Birch reduction of the intermediate amino alcohol yields XX A directly.

2-Substituted compounds (namely XX B) can be prepared from β-tetralone by removing the alcohol group by treatment with acidic reagents such as hydrochloric acid in acetic acid before the Birch reduction. Another method involves reaction of tetralones with a Wittic-type ylid to give side-chain nitriles which are reduced to primary amines and then substituted by well-known procedures to secondary or tertiary amines. A third process involves the Mannich bases derived from tetralones (i.e. reduction with LiAlH$_4$ followed by Birch reduction yields XX B $n'$=1). alternately quaternization followed by reaction with potassium cyanide or ethyl cyanacetate in the presence of base yields intermediates easily convertible to dihydronaphthalenes containing side-chain amines (i.e. XX A or XX B where $n'$=2 or 3 respectively). These are subjected to Birch reduction as above to yield hexahydronaphthalenes.

1,4,6,7,8,9-Hexahydro-5H-benzocycloheptenes of structures XX C, XX D and XX E

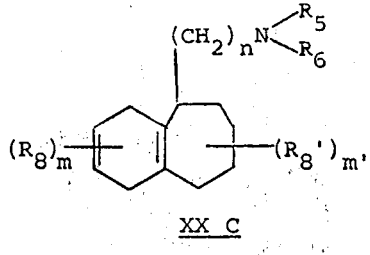

XX C

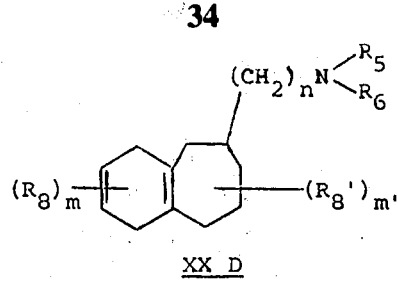

XX D

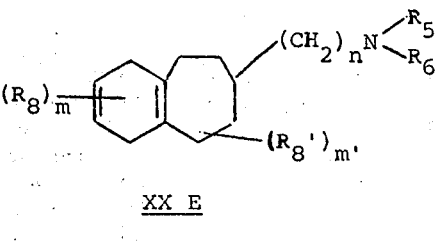

XX E may be prepared from the corresponding tetrahydro-5,6, or 7-H-benzocyclohepten-5,6, or 7-ones in several ways know in the art starting with the ketone shown below.

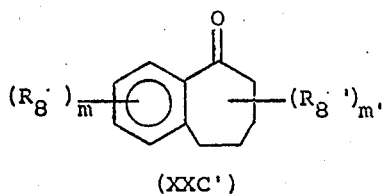

(XXC')

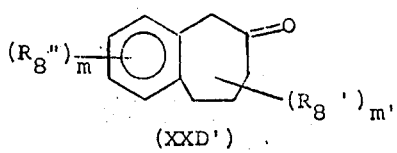

(XXD')

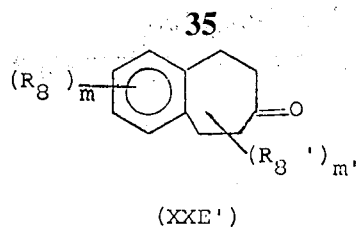

(XXE')

Reaction of the ketones with an aminoalkyl Grignard reagent followed, if necessary, by dehydration, and reduction provides the corresponding aminoalkyl 6,7,8,9-tetrahydro-5H-benzocycloheptene which is then subjected to a Birch reduction as described before. The starting ketones may also be reacted with a Wittig type ylid to produce side-chain nitriles which are reduced to primary amines and can then be substituted by standard procedures to secondary or tertiary amines before Birch reduction. Conversion of the starting ketones to oximes followed by reduction provides the corresponding primary amines where n=0 which then are reduced as above to the required dienes.

Intermediates

The dienes of the structure

II 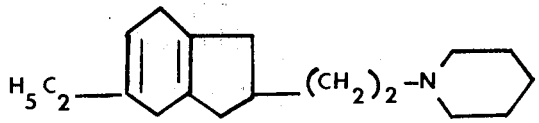

are novel intermediates. Examples of such dienes include the following:

1. 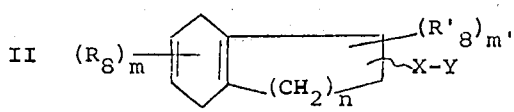

2. 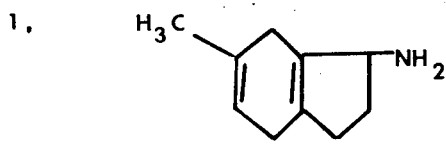

3. 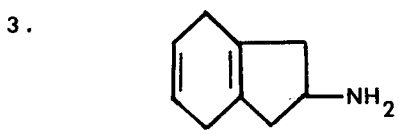

4. 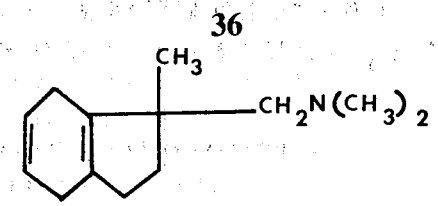

5. 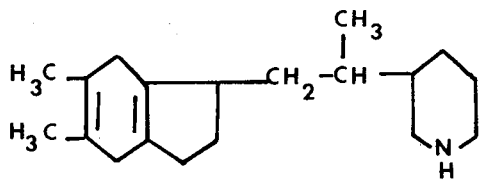

6. 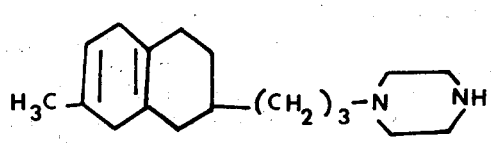

7. 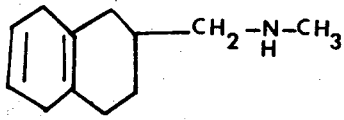

8. 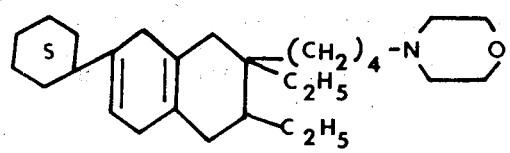

9. 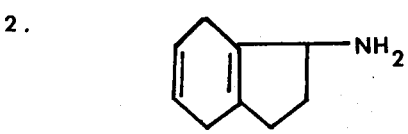

10. 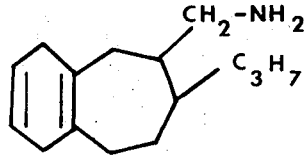

11. 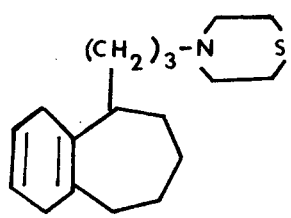

12.
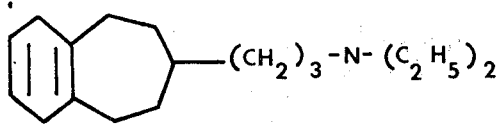
5.
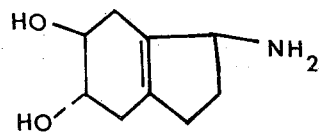
The diester and diol olefin intermediates of the structures:
VIII 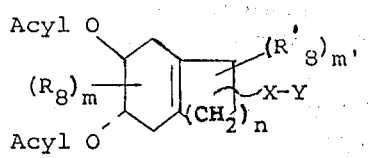
IX 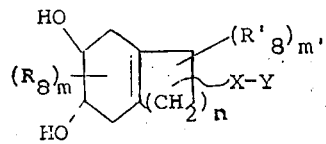
wherein acyl and X and Y are as defined hereinbefore are novel intermediates. Examples of such diesters or diol olefins include, but are not limited to
1.
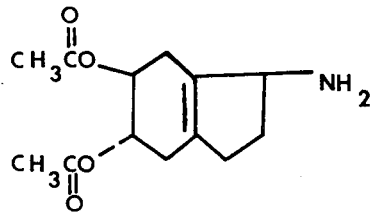
2.
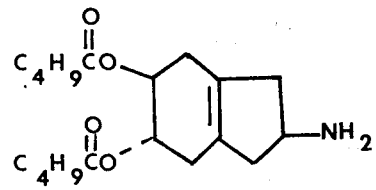
3.
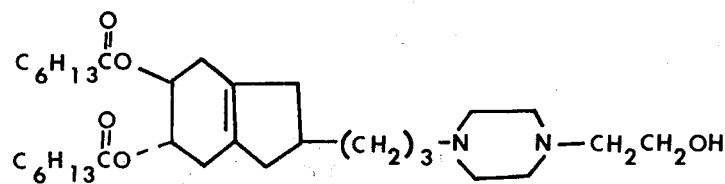
4.
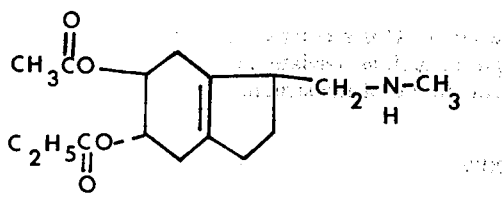
6.
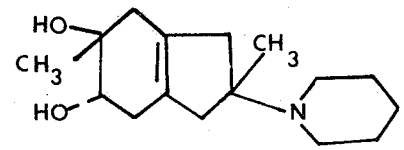
7.
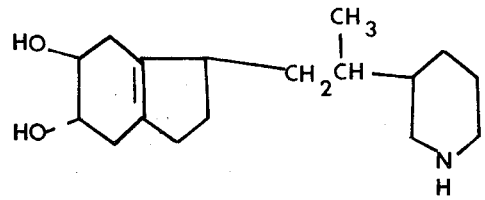
8.
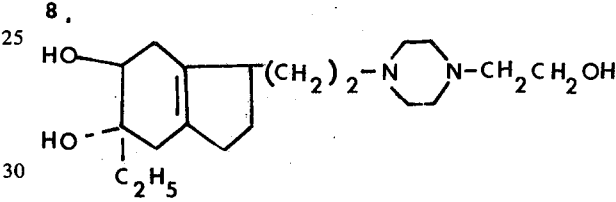
9.
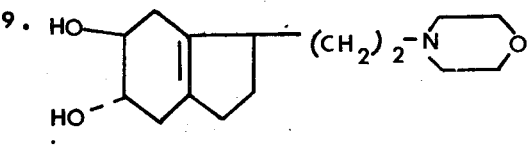
10.
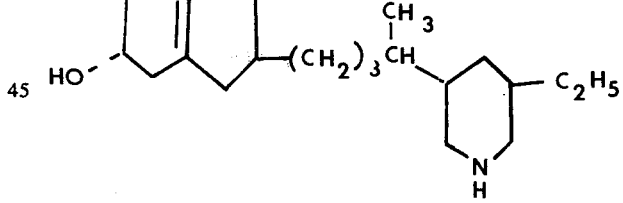
11.
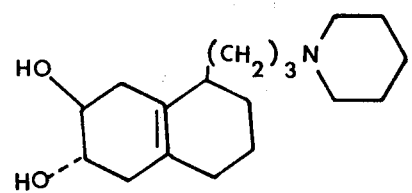

12. 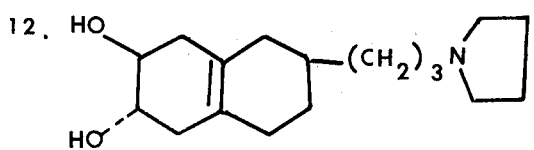

13. 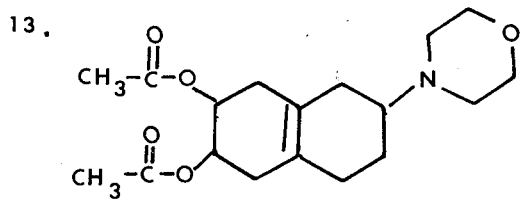

14. 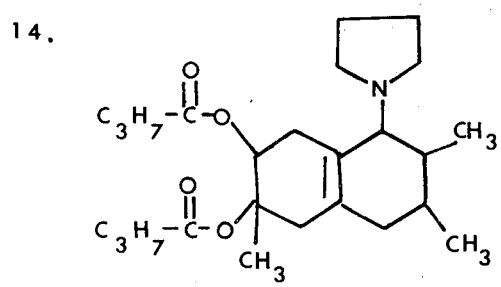

15. 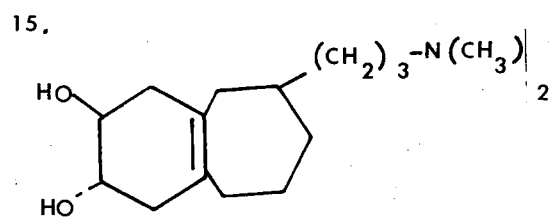

16. 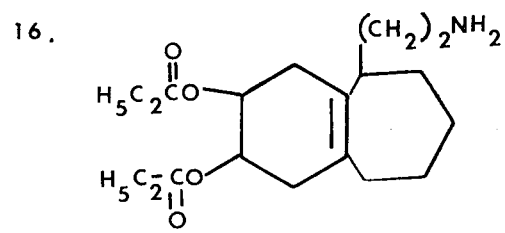

17. 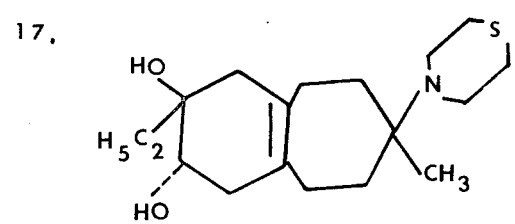

18. 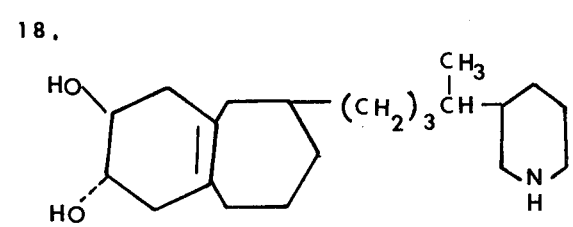

The diol olefins of the structure X that is

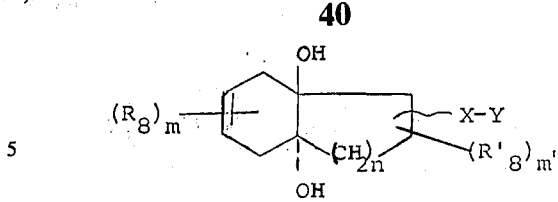

wherein X and Y are defined hereinbefore are novel intermediates.

Typical examples of diol olefins of the structure X correspond to the tetrols and esters and the diester and diol olefins of structure VIII and IX set out hereinbefore.

Preparation of Starting Materials

The diene intermediate:

XX 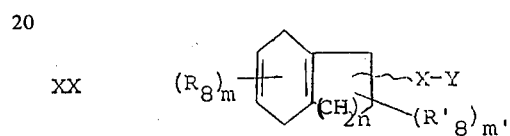

can be prepared by the Birch reduction of an aromatic precursor of the structure:

XXI 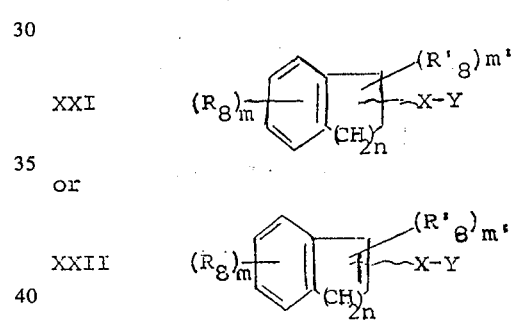

or

XXII

An aromatic indenyl precursor of the structure:

XXIII 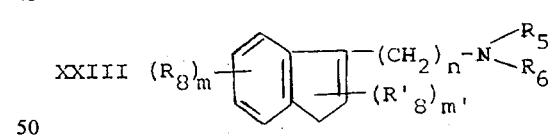

can be prepared by reacting an indene of the structure:

XXIV 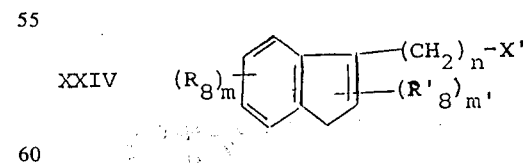

wherein X' is a reactive halogen or other displaceable group such as tosylate and $n$ is 1 to 10, with an amino compound of the structure:

XXV 

wherein $R_5$ and $R_6$ are as defined hereinbefore, in a molar ratio of indene:amine of within the range of from about 1:2 to about 1:10 and preferably from about 1:2 to about 1:4, at a temperature within the range of from about 75° to about 150° and preferably from about 100° to about 120°, in the presence of a solvent having a boiling point below about 150°C., such a toluene or xylene.

The aromatic indenyl precursor of the structure XXIII can be converted to the corresponding indanyl compound by reduction employing as a reducing agent, for example, hydrogen, in the presence of a catalyst for reduction, for example, platinum oxide.

The aromatic indenyl compounds of the structure XXIII can also be prepared by reacting indene with an amino alkylene halide of the structure:

XXVI  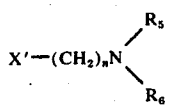

wherein X′, n, $R_5$ and $R_6$ are as defined hereinbefore, in the presence of a base, such as a concentrated aqueous solution of an alkaline earth metal hydroxide and Triton B in methanol, at a temperature within the range of from about 40° to about 75°C. and preferably from about 45° to about 55°C. The indene is employed in a molar ratio to halide of within the range from about 1:1 to about 10:1 and preferably from about 2:1 to about 4:1. The base is employed in a molar ratio to halide of within the range of from about 3:1 to about 10:1 and preferably from about 3:1 to about 5:1.

Indenyl compounds of the structure:

XXVII  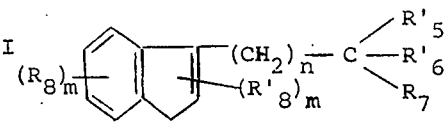

can be prepared by reacting an indene of the structure XXIV, i.e.,

with a compound of the structure:

XXVIII  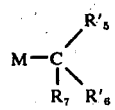

wherein M is an alkali metal, such as sodium or potassium, for example,

XXIX  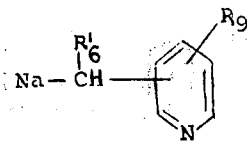

wherein $R_9$ can be any of the $R'_5$ groups, (molar ratio of indene to metal salt of within the range of from about 1:1 to about 1:10 and preferably from about 1:2 to about 1:4) in the presence of liquid ammonia. The resulting indenyl compound can be reduced to the corresponding indanyl compound by reacting with hydrogen in the presence of a catalyst for reduction such as platinum oxide.

Indenyl compounds of the structure:

XXX  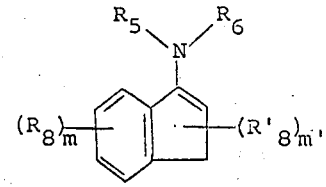

or

XXXI  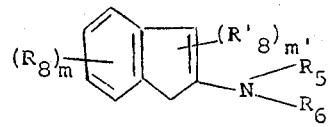

can be prepared by reacting a 1-indanone or 2-indanone with an amino compound of the structure XXV, i.e.,

(in a molar ratio of indanone:amine of within the range of from about 1:1 to about 1:4 and preferably from about 1:1.1 to about 1:1.5) in the presence of an aromatic solvent boiling below about 150°C. such as toluene or benzene, and p-toluenesulfonic acid, at a temperature of within the range of from about 80° to about 125°C. and preferably reflux temperature, removing water, solvent and excess amine reactant, dissolving the residue in an alcohol solvent boiling below about 100°C., such as methanol, and adding an alkali metal borohydride, an organic acid, such as acetic acid, to destroy remaining borohydride, and a base, to form the 1 or 2-indenyl compounds of structures XXX and XXXI.

Dihydronaphthalene and dihydrobenzosuberane starting materials of the structure:

XXXII  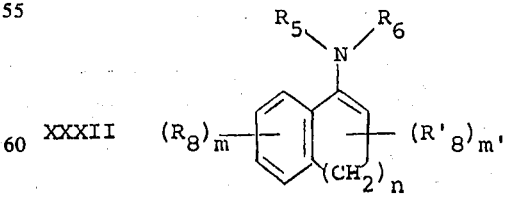

can be prepared by reacting 1-tetralone and an amino compound of the structure XXV, i.e.

(molar ratio tetralone:amine of 1:1.1 to about 1:1.5) in an aromatic solvent boiling below about 150°C., in the presence of p-toluenesulfonic acid, at a temperature within the range of from about 80° to about 140°C. and preferably from about 110° to about 140°C. to form the dihydronaphthalene.

The dihydronaphthalene can be converted to the corresponding tetrahydronaphthyl compound by reducing the salt form of the dihydro compound in the presence of a reducing agent, such as lithium aluminum hydride.

The aromatic precursor, i.e., the compounds of formulae XXI and XXII, respectively, undergo a Birch reduction to form the diene starting material of structure II. The Birch reduction is carried out by reacting the aromatic precursor with lithium in a molar ratio to the lithium of within the range of from about 1:2 to about 1:50 and preferably from about 1:10 to about 1:20 in the presence of liquid ammonia, a proton source such as a lower alcohol and ethyl ether as would be apparent to one skilled in the art.

Examples of aromatic starting materials of the structure:

XXIV 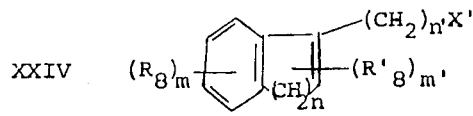

can be seen from Table A, wherein $m'=0$, and $n$, $n'$ and $X'$ in the above formula are defined.

Table A

| | | | | | |
|---|---|---|---|---|---|
| a) | $n' = 1$, | $X' = Cl$ | $n = 1$ | $m = 0$ | |
| b) | $n' = 2$, | $X' = Br$ | $n = 1$ | $m = 0$ | |
| c) | $n' = 2$, | $X' = I$ | $n = 2$ | $m = 1$ | $R_8 = 5\text{-}CH_3$ |
| d) | $n' = 4$, | $X' = p\text{-}CH_3C_6H_4SO_2O-$ | $n = 1$ | $m = 1$ | $R_8 = 6\text{-}C_2H_5$ |
| e) | $n' = 5$, | $X' = Cl$ | $n = 3$ | $m = 2$ | $R_8 = 5\text{-}CH_3,6\text{-}CH_3$ |
| f) | $n' = 6$, | $X' = Br$ | $n = 2$ | $m = 0$ | |
| g) | $n' = 07$, | $X' = Cl$ | $n = 3$ | $m = 1$ | $R_8 = 5\text{-}\langle S \rangle$ |
| h) | $n = 8$, | $X' = I$ | $n = 1$ | $m = 0$ | |

Examples of starting materials of the structure:

XXXV 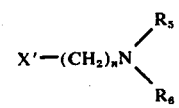

can be seen from Table B wherein $R_5$ and $R_6$ are defined.

Table B

| | $R_5$ | $R_6$ |
|---|---|---|
| a) | 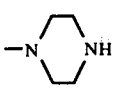 |  |
| b) | $CH_3-$ | $C_2H_5$ |
| c) | $H$ | $CH_3$ |
| d) | $ClCH_2-$ | $ClCH_2-$ |
| e) | 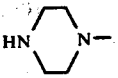 | |

Table B-continued

| | $R_5$ | $R_6$ |
|---|---|---|
| f) |  |  |
| g) | 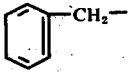 | 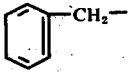 |
| h) | 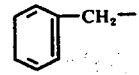 | 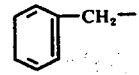 |
| i) | $CH_3$ | $CH_3$ |
| j) | $C_2H_5$ | $C_2H_5$ |

Examples of starting materials of the structure:

XXVI $X'-(CH_2)_nN\begin{smallmatrix}R_5\\R_6\end{smallmatrix}$ can be seen from Table C wherein $X'$, $n'$, $R_5$ and $R_6$ are defined.

Table C

| | $X'$ | $n'$ | $R_5$ | $R_6$ |
|---|---|---|---|---|
| a) | Br | 2 | $C_2H_5$ | $CH_3$ |
| b) | Cl | 2 | $CH_3-\overset{O}{\underset{\|}{C}}-$ | $CH_3\overset{O}{\underset{\|}{C}}-$ |
| c) | Br | 3 |  |  |
| d) | I | 4 |  |  |
| e) | Cl | 5 | $HO-CH_2CH_2-$ | $HOCH_2CH_2-$ |
| f) | I | 10 | 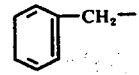 | 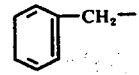 |

Examples of starting materials of the structure:

XXVIII 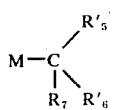

can be seen from Table D wherein M, $R'_5$, $R'_6$ and $R_7$ are defined.

Table D

| | M | $R'_5$ | $R'_6$ | $R_7$ |
|---|---|---|---|---|
| a) | K | $C_2H_5$ | $C_2H_5$ | H |
| b) | Na | | (tetrahydropyran-yl, O) | H |
| c) | Li | (morpholinyl, N-O) | (morpholinyl, N-O) | H |
| d) | Na | | (cyclopropyl) | H |
| e) | K | H | (tetrahydropyran-yl, O) | |
| f) | Na | (phenyl) | (phenyl) | $-CH_3$ |

The following Examples further illustrate the invention.

EXAMPLE 1

1-[3-(4,7-Dihydro-1-indanyl)propyl]piperidine hydrobromide

Crude 1-[3-(4,7-dihydro-1-indanyl)propyl]piperidine is prepared in 99% yield by the Birch reduction of 1-[3-(3-indenyl)propyl]piperidine as follows:

A solution of 13.5 g. (0.056M) 1-[3-(3-indenyl)propyl]piperidine in 100 ml. ether is added to 1 l. liquid ammonia and 100 ml. ether. Lithium ribbon (20.0 g., 2.85 M) is added in several portions over a period of 15 minutes while stirring. The mixture which is a greenish-bronze is stirred for 1½ hours and absolute ethanol is added dropwise until the color is discharged.

After the ammonia has evaporated, the residue is diluted to 1500 ml. with water and extracted two times with ether. The ether extracts are dried over potassium carbonate and the solvent is removed in vacuo leaving 13.9 g. (100% yield) of diene identified as 1-[3-(4,7-dihydro-1-indanyl)propyl]piperidine.

A 5.0 g. sample of the diene is converted to the hydrobromide by dropwise addition of a hydrobromic acid solution to a solution of the diene until a pH of 4 is reached (pH meter). Removal of the solvent and crystallization of the crude yellow solid from ethanol-ether gives 3.8 g. (56%) of crystalline hydrobromide. One more recrystallization from the same solvent mixture yields 2.4 g. (35%) 1-[3-(4,7-dihydro-1-indanyl)-propyl]piperidine hydrobromide, dec. 188°–196°C.

Analysis: Calc'd for $C_{17}H_{27}N\cdot HBr$: C, 62.57; H, 8.65; N, 4.29 Br, 24.49 Found: C, 62.70; H, 8.60; N, 4.04 Br, 24.51.

EXAMPLE 2

3a,7a-trans-5,6-trans-Hexahydro-1-(2-piperidinoethyl)-3a,5,6,7a-indantetrol 2-(1-Indenyl)ethanol The above compound is prepared as described by Howell & Taylor, J.C.S., 1957, 3013. To butyl-lithium, prepared from lithium (20.0 g.) and butyl bromide (234 g.) in ether, indene (116 g., 1.0 M) is added with stirring under nitrogen at −10°. After 1 hour at −10° ethylene oxide (88 g.) in ether (300 ml.) is added in one-half hour. After warming to 10°, 500 ml. water is added cautiously and stirring is continued until there is no lithium remaining. The layers are separated and the organic layer is washed once with dilute HCl and three times with water. After drying, the ether is removed and the product distilled, collecting 76 g. (48%) at 125–135/0.2 mm. N.M.R. establishes the position of the double bond as 2,3.

2-(1-Indenyl)ethyl tosylate

The alcohol described above (49 g., 0.306 M) is mixed with 64.8 g. (0.350 M) p-toluenesulfonyl chloride. The paste is cooled to 0° and pyridine (49 g., 0.62 M) is added dropwise over a period of 1 hour. The cold solution is stirred for 4 hours before an excess of dilute HCl is added. The product is extracted with ether yielding 95 g. (99+%) viscous tosylate. N.M.R. establishes the position of the double bond as 2,3.

1-[2-(3-Indenyl)ethyl]piperidine

The crude tosylate (41.5 g., 0.13 M) and piperidine (28 g., 0.33 M) in 200 ml. toluene are heated under reflux overnight. Ether is added to the warm reaction mixture until crystals begin forming. After cooling, the solid is removed by filtration and washed several times with ether. The filtrate and washes are combined and the solvents removed in vacuo. The oily residue is dissolved in ether, a small amount of insoluble material is removed by filtration, and the ether is removed from the filtrate leaving 29.7 g. (99%) of brown oil. The sample is purified by distillation at reduced pressure recovering 86% as a yellow oil boiling 115°/0.05 mm. to 130°/0.1 mm.

A solution of 15.0 g. (0.066 M) 1-[2-(3-indenyl)ethyl]piperidine in 100 ml. ether is added to 1 l. liquid ammonia and 100 ml. ether. Lithium ribbon (20.0 g., 2.85 M) is added in several portions over a period of 15 minutes while stirring. The greenish-bronze mixture is stirred 1½ hours. Absolute ethanol is added dropwise until the color is discharged (260 ml. required, added over a period of 1 hour 40 minutes). After the ammonia has evaporated, the residue is diluted to 1500 ml. with water and extracted two times with ether. The ether extracts are dried over potassium carbonate and the solvent is removed in vacuo leaving 13.1 g. (86% yield) of amber colored oil. Comparison of the IR and UV of the product with those of the starting material indicates no starting material remains. The product is identified as 1-[2-(4,7-dihydro-1-indanyl)ethyl]piperidine.

The diene (11.0 g., 0.048 M) is added dropwise over a period of 15 minutes to 100 ml. cold 98% formic acid. This is followed by dropwise addition (40 minutes) of 57 ml. (∼ 0.5 M) 30% hydrogen peroxide maintaining a temperature of 20°C. The temperature is then allowed to rise to 35° and is held at 30°–35°, using a large water bath, for 4 hours before the mixture is left stirring overnight. The reaction mixture is taken to near dryness and any residual performic acid is removed by twice adding water and removing in vacuo.

The remaining yellow oil is dissolved in 100 ml. absolute ethanol and a solution of 30 g. KOH in 50 ml. water is added. The mixture is heated under reflux one hour, cooled, and diluted to 500 ml. with water. This is extracted four times with ether. The ether extracts are dried over magnesium sulfate, filtered, and the ether is removed in vacuo leaving 7.2 g. (51%) yellow-tan solid. Two recrystallizations from ethyl acetate give 4.25 g. (30% yield) of 3a,7a-trans-5,6-trans-hexahydro-1-(2-piperidinoethyl)-3a,5,6,7a-indantetrol melting 179°–182°C.

Analysis: Calc'd for $C_{16}H_{29}NO_4$: C, 64.18; H, 9.79; N, 4.68. Found: C, 64.21; H, 9.82; N, 4.68.

EXAMPLE 3

3a,7a-trans-5,6-trans-Hexahydro-1-(2-piperidinoethyl)-3a,5,6,7a-indantetrol-5,6-diacetate hydrochloride 3a,7a-trans-5,6-trans-Hexahydro-1-(2-piperidinoethyl)-3a,5,6,7a-indantetrol, as prepared in Example 2, (2.0 g., 0.0067 mole) is dissolved in 35 ml. pyridine. While cooling in an ice bath, acetic anhydride (18 ml.) is added dropwise over a period of 30 minutes. After stirring overnight at room temperature, the mixture is taken to dryness in vacuo. The residue is dissolved in chloroform and extracted two times with 5% $K_2CO_3$ solution. The chloroform solution is dried over magnesium sulfate, filtered, and the chloroform is removed in vacuo. Benzene is added two times and removed in vacuo to free the sample of any residual pyridine. The remaining foamy material is dissolved in an isopropanol-ether mixture and converted to the hydrochloride by addition of a solution of HCl in isopropanol yielding 1.5 g. (54%) of the above-titled compound, m.p. 262°–263°C. Recrystallization from an ethanolisopropanol mixture gives 1.0 g. (36%) of the above-titled compound, m.p. 262°–263°C.

Analysis: Calc'd for $C_{20}H_{33}NO_6 \cdot HCl$: C, 57.21; H, 8.16, N, 3.33 Cl, 8.44. Found: C, 57.13; H, 8.27, N, 3.18 Cl, 8.66.

EXAMPLE 4

3a,7a-trans-5,6-trans-Hexahydro-1-(5-piperidinopentyl)-3a,5,6,7a-indantetrol 3,5'-Bromopentylindene The compound is prepared as reported by Makoska in Tetrahedron Letters, 38, 4621–4624 (1966) by adding a mixture of equal molar quantities of indene and 1,5-dibromopentane to 50% aqueous NaOH containing methanolic Triton B. An oil forms which is purified by distillation. The material boiling at 141°–147°C., 0.1 mm is collected (~50% yield) and identified as 3,5'-bromopentylindene.

1-[5-(Inden-3-yl)pyridinium bromide

A mixture of the 3,5'-bromopentylindene (as prepared above) (85 g., 0.32 mole) and 28 g. (.35 mole) pyridine in 100 ml. acetonitrile is refluxed 20 hours. A small amount of ether is added to the warm reaction mixture (to turbidity). After further cooling, the crystalline product (107.5 g., 98%) is removed by filtration and washed with ether, m.p. 142°–146°C. and identified as 1-[5-(inden-3-yl)pentyl]pyridinium bromide.

1-[5-(Indan-1-yl)pentyl]piperidine

The 1-[5-(inden-3-yl)pentyl]pyridinium bromide described above (106 g., 0.31 mole) is hydrogenated on a Paar apparatus as follows. The bromide is divided up into four parts and fed into four bottles. Two hundred ml. methanol, and 0.6 g. platinum oxide catalyst are added to each bottle. Uptake of hydrogen is complete at room temperature within 75 minutes and agrees with theory for reduction of four double bonds. The catalyst is removed by filtration and the solvent is removed. The product is crystallized from a mixture of ethanol-ether (3:1) to give 103.6 g. (96%) of crystalline 1-[5-indanyl-1-yl)pentyl]piperidine hydrobromide, m.p. 147°–152°C.

The hydrobromide is converted quantitatively to the free base by basifying an aqueous solution of the hydrobromide, extracting the free base with ether, drying the ether solution and finally removing the ether at reduced pressure.

3a,7a-trans-5,6trans-Hexahydro-1-(5-piperidinopentyl)-3a,5,6,7a-indantetrol

A solution of 16.3 g. (.06 M) of the free 1-[5-(indan-1-yl)pentyl]piperidene base described above in 100 ml. ether is added to 1 l. liquid ammonia and 100 ml. ether. While the mixture is stirred, 20.0 g. (2.85 M) lithium ribbon is added in several portions over a period of 15 minutes. The bronze-blue mixture obtained is stirred 45 minutes. Absolute ethanol is added dropwise until the blue color is discharged (375 ml. required, added over a period of 2 hours).

The ammonia is evaporated. The residue is diluted to 1500 ml. with water and extracted three times with ether. The ether extracts are dried over potassium carbonate and the ether is removed in vacuo leaving 16.2 g. (99%) of oil. Comparison of IR and UV of the product and starting material indicates no starting material remained.

The oil (16.2 g., 0.06 M) is added dropwise over a period of 15 minutes to 100 ml. cold 98% formic acid. This is followed by dropwise addition (25 minutes) of 59 g. (.5 M) 30% hydrogen peroxide maintaining a temperature of 20°. The temperature is then allowed to rise to 35° and is held at 30°–35°, using a large water bath, for 3 hours. It is then left stirring overnight. The reaction mixture is taken to near dryness. Any residual performic acid is removed by twice adding water and removing in vacuo.

The remaining yellow oil is dissolved in 100 ml. absolute ethanol. A solution of 30 g. KOH in 50 ml. water is added. The mixture, which darkens immediately, is refluxed one hour. After cooling the mixture is diluted to 500 ml. with water. Crude brown viscous product (12.4 g., 61%) is obtained by extracting with ether. Crystallization from ethyl acetate and two recrystallizations from the same solvent with charcoal treatment yields a white crystalline product (3.2 g., 16%) melting 153°–156°C. identified as 3a,7a-trans-5,6-trans-hexahydro-1-(5-piperidinopentyl)-3a,5,6,7a-indantetrol Analysis: Calc'd for $C_{19}H_{35}NO_4$: C, 66.82; H, 10.33; N, 4.10. Found: C, 66.90; H, 10.43; N, 4.04.

EXAMPLE 5

3a,7a-trans-5,6-trans-Hexahydro-1-(5-piperidinopentyl)-3a,5,6,7a-indantetrol, 3a,5,6,7a-tetraacetate 3a,7a-trans-5,6-trans-Hexahydro-1-(5-piperidinopentyl)-3a,5,6,7a-indantetrol as prepared in Example 4 (4.0 g., 0.012 mole), is added to 80 ml. acetic anhydride. Glacial acetic acid (5 ml.) is added to give a clear solution. While cooling the solution in an ice-salt bath, 70% perchloric acid (8 ml.) is added dropwise over a period of 0.5 hour. The mixture is kept at about −15°C. for 16 hours. Cooling is continued during a dropwise addition of methanol (80 ml., 0.5 hour). After basificaion with concentrated ammonium hydroxide, the mixture is extracted three times with chloroform. The combined chloroform extracts are dried over magnesium sulfate, filtered, and the chloroform is removed in vacuo leaving 5.2 g. amber colored viscous material. Most of this material is dissolved in hot hexane (200 ml.). After cooling, 1.5 g. of crystalline product (the above-titled compound) (Crop I) is harvested by filtration, m.p. 123°–130°C. Concentraion of mother liquor yields several additional crops totaling about 1.6 g. [yield of crude crystalline material (the above-titled compound) 3.1 g., about 50% theory].

The Crop I material is recrystallized from hexane to give 1.3 g. (21% yield) melting 123°–128°C.

Analysis: Calc'd for $C_{27}H_{43}NO_8$: C, 63.63; H, 8.51; N, 2.75; Found: C, 63.79; H, 8.50; N, 2.82;

EXAMPLE 6

3a,7a-trans-5,6-trans-Hexahydro-1-(5-piperidinopentyl)-3a,5,6,7a-indantetrol-5,6-diacetate, hydrochloride 3a,7a-trans-5,6-trans-Hexahydro-1-(5-piperidinopentyl)-3a,5,6,7a-indantetrol as prepared in Example 4 ((4.0 g., 0.012 mole), is dissolved in 70 ml. pyridine. The solution is cooled in an ice bath and acetic anhydride (35 ml.) is added dropwise over a period of 30 minutes. The mixture is stirred overnight at room temperature, then taken to near dryness in vacuo. The residue is dissolved in chloroform and extracted two times with 5% $K_2CO_3$. The chloroform solution is dried over magnesium sulfate, filtered, and the chloroform is removed in vacuo, leaving an oily material. Benzene is added two times and removed in vacuo to free the sample of any residual pyridine.

The oil is dissolved in ether, filtered to remove a small amount of insoluble material, and converted to the hydrochloride by addition of a solution of HCl in isopropyl alcohol yielding 4.4 g. (80%). Two recrystallizations from isopropanol-ether give 2.05 g. (38%) of the above-titled compound melting at 209°–210°C.

Analysis: Calc'd for $C_{23}H_{39}NO_6 \cdot HCl$: C, 59.79; H, 8.73; N, 3.03; Found: C, 59.75; H, 8.93; N, 3.00;

EXAMPLE 7

3a,7a-trans-5,6-trans-Hexahydro-1-(3-morpholinopropyl)-3a,5,6,7a-indantetrol

1-[3-(3-Indenyl)propyl] morpholine 3,3′ Bromopropylindene (23.7g, 0.1M), morpholine (22g, 0.25M) and 100 ml toluene are heated under reflux for 2 hours. After cooling, a large amount of solid is removed by filtration and washed with ether. The filtrate is concentrated in vacuo. The residue is dissolved in ether and filtered to remove a small amount of insoluble material. The ether is removed and the product is distilled collecting 22.0g (90%) boiling point 152–162/0.05mm. of the above tilled compound.

A sample of this material is converted to the hydrochloride m.p. 192°–194°C.

Analysis: Calc'd: C, 68.68; H, 7.93; N, 5.02; Cl, 12.67. Found: C, 68.92; H,8.02; N,5.10; Cl,12.41.

3a, 7a-trans-5,6-trans-Hexahydro-1-(3-morpholinopropyl)-3a,5,6,7a-indantetrol

A solution of 1-[3-(3-indenyl)propyl]morpholine(16.5g, 0.068M), as prepared above in 100 ml ether is added to 1 l liquid ammonia and 100ml ether. Lithium ribbon (25g.) is added in several portions over a period of 20 minutes. The greenish brown mixture is stirred 2 hours. Absolute ethanol is added dropwise until the color is discharged (225ml required added over a period of 2 hours). After the ammonia has evaporated, the residue is diluted to 1500ml with water and extracted three times with ether. The ether extracts are dried over potassium carbonate and the solvent is removed in vacuo leaving an amber oil. The UV on the amber oil (16.6g,100%) indicated no starting material remained. The amber oil is identified as 1-[3-(4,7-dihydro-1-indanyl)propyl] morpholine.

The crude diene (0068M) is added dropwise over a period of 15 minutes to 100ml cold 98% formic acid. This is followed by dropwise addition (40 minutes) of 60ml 30% hydrogen peroxide maintaining a temperature of 20°. The temperature is then allowed to rise to 35° and held at 30°–35° using a large water bath, for 3 hours. The mixture is stirred overnight in the bath. The reaction mixture is taken to near dryness and any residual performic acid is removed by twice adding water and removing in vacuo.

The viscous residue is then dissolved in 75ml absolute ethanol and treated with a solution of 30g. potassium hydroxide in 50ml water. After heating under reflux for one hour, the mixture is diluted to 500ml with water. Four ether extracts yields 2.3g. yellow oil (Fraction A). The aqueous solution is then set up for continuous extraction with ethyl acetate. After 2½ hours 7.3g of (Fraction B) material is extracted. Overnight extraction yields an additional 3.5g (Fraction C). Total aount extracted 13.1g (61%). From an ethyl acetate solution of (Fraction B) there is obtained 5.2g. of crystalline material which is recrystallized from ethyl acetate to give 3a, 7a-trans-5,6-trans-hexahydro-1-(3-morpholinopropyl)-3a,5,6,7a - indantetrol (4.2g, 20%) m.p. 148°–151°C.

Analysis: Calc'd for $C_{16}H_{29}NO_5$: c, 60.93; H,9.27; N,4.44. Found: C,60.86; H, 9.03; N, 4.36;

EXAMPLE 8

3a,7a-trans-5,6-trans-Hexahydro-1-(3-morpholinopropyl)-3a,5,6,7a-indantetrol, 3a,5,6,7a tetra-acetate 3a,7a-trans-5,6-trans-Hexahydro-1-(3-morpholinopropyl)- 3a,5,67a-indantetrol as prepared in Example 7, (1.5g.,0.0048 mole) is added to 30ml acetic anhydride. Glacial acetic acid (about 1ml) is added dropwise to give a clear solution. While cooling in an ice-salt bath, 70% perchloric acid (3ml) is added dropwise over a period of 15 minutes. The mixture is kept at −15°C for 20 hours. Cooling is continued during dropwise addition of methanol (30ml in 25 minutes). After basification with concentrated ammonium hydroxide, the mixture is extracted three times with chloroform. The combined chloroform extracts are dried over magnesium sulfate, filtered, and the solvent removed in vacuo leaving 2.35g of amorphous material. Crystallization from hexane yields 1.35g. (58%) of material melting 144°–147°C. This is recrystallized from the same solvent yielding 950mg (41%) of the above titled compound melting at 145°–148°C.

Analysis: Calc'd for $C_{24}H_{37}NO_9$: C, 59.62; H, 7.71; N,2.90; Found: C, 59.89; H, 7.52; N,2.90;

EXAMPLE 9

3a,7a-trans-5,6-trans-Hexahydro-1-(3-morpholinopropyl)-3a,5,6,7a-indantetrol,5,6-diacetate 3a,7a-trans-5,6-trans-Hexahydro-1-(3-morpholinopropyl)-3a,5,6,7a-indantetrol, as prepared in Example 7, (1.9g, 0.006 mole) is dissolved in 35ml pyridine. The solution is cooled in an ice bath and acetic anhydride (18ml.) is added dropwise over a period of 30 minutes. The mixture is stirred overnight at room temperature, then taken to dryness in vacuo. The residue is dissolved in chloroform and extracted three times with 5% $K_2CO_3$ solution. The chloroform solution is dried over magnesium sulfate, filtered and the chloroform is removed in vacuo. The sample is freed of any residual pyridine by twice adding benzene and removing in vacuo. Most of the product is not soluble in 75ml hot benzene and 1.95g (81%) of crystalline material is removed by filtration. Two recrystallizations from acetone yielded the above titled compound, 900mg. (38%) melting at 100°–125°C.

Analysis: Calc'd for $C_{20}H_{33}NO_7$: C, 60.13; H, 8.33; N, 3.51; Found: C, 59.92; H, 8.45, N.3.53;

EXAMPLE 10

2,3a,5-cis-6,7-trans-Hexahydro-2-piperidino-3a,5,6-,7a-indantetrol 1-(2-Indanyl)piperidine A mixture of 79g (0.6mole) of β-indanone and 100 ml. of piperidine in 500 ml. of benzene is treated with 0.5g p toluenesulfonic acid and heated under reflux with a water take-off trap attached. Heating continued 3 hours, no additional water being collected near the end of this period. The solvent and excess piperidine is then removed in vacuo. The residue is dissolved in 1 l. of absolute methanol and, while the temperature is maintained below 30°C, 40g. of sodium borohydride ($NaBH_4$) is added in several portions. The mixture is allowed to stir an additional two hours and then a small amount of acetic acid is added to destroy any $NaBH_4$ remaining. The mixture is then made strongly basic by adding NaOH solution, 250 ml. of water is added, and most of the methanol is removed in vacuo. The product is extracted with three portions of ether, the extracts dried over KOH and the ether is removed in vacuo. The product (1-(2-indanyl) piperidine) is distilled, collecting 107g(89%) boiling 125°–130°C/1.0 mm. which solidifies on standing.

A small amount of this material is converted to the hydrochloride. After two recrystallizations from 2-propanol the material, mp. 257°–259°C, analyzed as follows:

Analysis: Calc'd: C, 70.72; H, 8.48; N, 5.89; Cl, 14.91; Found: C, 70.75; H, 8.49; N, 5.93; Cl, 14.96;

1-(4,7-Dihydro-2-indanyl) piperidine

A solution of the distilled -1-(2-Indanyl)piperidine (40.2g, 0.2M) in 350 ml ether is added to 2.5 l liquid ammonia and 250 ml. ether. Lithium ribbon (50g.) is added in several portions over a period of 20 minutes. The blue-bronze mixture is stirred 30 min. before absolute ethanol is added dropwise until the color is discharged (475 ml. required, added over a period of two hours). After the ammonia has evaporated, the residue is cooled and diluted to about 4 l. with water, and then extracted two times with ether. The ether extracts are dried over potassium carbonate and the solvent is removed in vacuo leaving 41g (100% yield) of 1-(4,7-dihydro-2-indanyl)piperdine) which solidifies on standing. The UV indicates no starting material remains.

A sample of this material is converted to the hydrobromide. After two recrystallizations from 2-propanol, the material. dec:244–246 analyzes as follows:

Analysis: Calc'd: C, 59.16; H, 7.80; N, 4.93; Br, 28.11; Found: C, 59.14; H, 7.73; N, 4.87, Br, 28.06;

2,3a,5-cis-6,7-trans-Hexahydro-2-piperidino-3-,5,6,7a-indantetrol

The crude diene as prepared above (37g, 0.18M) is added in several portions to 300 ml cold 98% formic acid. This is followed by dropwise addition (1 hour) of 30% hydrogen peroxide (170ml.) maintaining the temperature at 20°–25°C. The temperature is then allowed to rise to 35° and is held at 30°–35°, using a large water bath, for 3 hours before the mixture is left stirring overnight, in the bath. The reaction mixture is taken to near dryness and any residual performic acid is removed by twice adding water and removing in vacuo.

The viscous residue is then dissolved in 300 ml. absolute ethanol and treated with a solution of 90g. KOH in 100 ml. water. After hating under reflux one hour the dark-brown mixture is diluted to 1 l. with water. Four extractions with ether and three with ethyl acetate yields a total of 32.3g. (about 66%) of partially crystalline material. Heating the material with benzene and ethyl acetate gives 22.4g (46% yield) crystalline material. A portion of this material is recrystallized two times from 2-proponel to give 2,3a,5-cis-6,7a-trans-hexahydro-2-piperidino-3a,5,6,7a-indantetrol, m.p. 238°–241°C.

Analysis: Calc'd: C, 61.96; H, 9.29; N, 5.16; Found: C, 61.90; H, 9.28; N, 5.10;

EXAMPLE 11

3a,7a-trans-5,6-trans-Hexahydro-2-piperidino-3a,5,6,7a-indantetrol, 5,6-dibenzoate.

2,3a,5-cis-6,7a-trans-Hexahydro-2-piperidino-3a,5,6,7a-indantetrol, as prepared in Example 10, (2.0 g., 0.0073M) is partially dissolved in 25 ml. pyridine and 6 ml. benzoyl chloride is added. The dark reaction mixture is heated on a steam bath for 1 hour. The solvent is removed in vacuo and the residue is treated with saturated $NaHCO_3$ solution. The product is extracted with chloroform. The dark brown viscous material remaining after removal of the solvent is chromatographed on neutral alumina-activity grade IV. The product (1.45 g., 41%) is eluted with ether and recrystallized from ether-pet ether to yield the above titled compound, 1.0 g. (28%) m.p. 146°–147.5°C.

Analysis: Calc'd for $C_{28}H_{33}NO_6$: C, 70.12; H, 6.94; N, 2.92; Found: C, 70.12; H, 7.08; N, 2.63.

EXAMPLE 12

2,3a,5-cis-6,7a-trans-Hexahydro-2-piperidino-3a,5,6-,7a-indantetrol, 3a, 5,6-triacetate, hydrochloride.

2,3a,5-cis-6,7a-trans-Hexahydro-2-piperidino-3a,5,6,7a-indantetrol, as prepared in Example 10 (4.0g; 0.0147 mole) is partially dissolved in 70 ml. pyridine. The mixture is cooled in an ice bath and acetic anhydride (35ml) is added dropwise over a period of 40 minutes. The mixture is stirred overnight at room temperature. The clear amber solution is then taken to dryness in vacuo. The residue is dissolved in chloroform and extracted two times with 5% $K_2CO_3$ solution. The chloroform solution is dried over $MgSO_4$, filtered, and the solvent is removed in vacuo. The sample is freed of any residual pyridine by twice adding benzene and removing in vacuo. Crystallization from benzene-pet ether yielded (2S, - 3aR, 5S, 6S, 7aR)-hexahydro-2- piperidino-3a,5,6,7a-indantetrol-3a,5,6-triacetate, 2.05 g. (35%) melting at 126°–141°C.

A portion of this material is converted to the hydrochloride. Two recrystallizations from isopropanol gives the above-titled compound melting at 236°–237°C (dec.).

Analysis, Calculated for $C_{20}H_{31}NO_7 \cdot HCl$: C, 55.36; H, 7.43; N, 3.23; Cl, 8.17; Found: C, 55.60; H, 7.56; N, 3.32, Cl, 8.20.

EXAMPLE 13

3a,7a-trans-5,6-trans-Hexahydro-2-piperidino-3a,5,6-,7a-indantetrol, 5,6-diacetate and 2,3a,5-cis-6,7a-trans-hexahydro-2-piperidino-3a,5,6-,7a-indantetrol,3a,5,6-triacetate.

A mixture of 210 ml. pyridine and 105 ml. acetic anhydride are stirred and cooled in an ice-water bath. A 2,3a,5-cis-6,7a-trans-hexahydro-2-piperidino-3a, 5, 6, 7a-indantetrol (12.5 grams, 0.046 mole) is added slowly with stirring. The ice bath is removed and the solution allowed to stir overnight at room temperature.

A portion of the solution is evaporated to an oil. Benzene is added and evaporated twice in vacuo. Addition of ethyl acetate affords a yellow solid, 3a, 7a-trans-5,6-trans-hexahydro-2-piperidino-3a, 5, 6, 7a-indantetrol, 5,6-diacetate, hydroacetate (10.34 grams, 54% yield).

A portion of the solution is diluted with three volumes of methylene chloride. Filtering yields a yellow solid, the hydroacetate of the free base of 2,3a,5-cis-6,7a-trans-hexahydro-2-piperidino-3a, 5, 6, 7a-indantetrol 3a, 5, 6-triacetate (4.20 g., 20%).

Each product is converted to the respective free base by treatment with saturated bicarbonate solution, extraction with methylene chloride and evaporation in vacuo.

From 2.95 grams of hydroacetate of free base of 2,3a,5-cis-6,7a-trans-hexahydro-2-piperidino-3a, 5, 6, 7a-indantetrol 3a, 5,6-triacetate is obtained 2.93 grams crude free base.

From 7.15 grams of diacetate hydroacetate is obtained 5.33 grams (87.0%) free base after crystallization from hot ethyl acetate. A 3.65 g. sample (m.p. 126.5°–129.5°C) is recrystallized from hot ethyl acetate to afford 2.21 g. of analytical sample (m.p. 128°–131°C).

EXAMPLE 14

3a, 7a-trans-5,6-trans-Hexahydro-2-piperidino-3a, 5, 6, 7a-indanetetrol, 3a, 5-diacetate A 3.33g., (0.00837 mole) sample of the free base of 2,3a,5-cis-6,7a-trans-hexahydro-2-piperidino-3a, 5, 6, 7a-indantetrol-3a, 5, 6-triacetate is allowed to stand overnight at room temperature in 850 ml. of methanol:-water (9:1). The solution is evaporated and the residue taken up in methylene chloride. The solution is shaken vigorously with saturated sodium bicarbonate solution. The organic layer is separated, dried ($Na_2SO_4$) and evaporated to an oil which yields 1.77 g. (m.p. 183°–185°C) on crystallization from hot ethyl acetate. A second crystallization from hot ethyl acetate affords the above-titled compound (m.p. 184.5°–185.5°C).

EXAMPLE 15

2,3a,5-cis-6,7a-trans-hexahydro-2-piperidino-5,6,7a-indantetrol-3a-monoethyl ester hydrochloride A solution of 800 ml. of ethyl ether and 2 g. of 2,3a,5-cis-6,7a-trans-hexahydro-2-piperidino-3a, 5, 6, 7a-indantetrol is treated with 80 ml. of chloroethylcarbonate. A precipitate forms. The mixture is stirred overnight at room temperature. The solid is filtered off and collected (1.7g.).

The filtrate is evaporated and the residue is treated with acetone. The resulting solid (0.1g.) is identical with the first solid.

The combined fractions are recrystallized from methanol and ether and the above-titled compound is obtained (m.p. 193–4).

Analysis, Calculated for $C_{17}H_{30}NO_6Cl$: C, 53.76; H, 7.96; N, 3.69; Cl, 9.33. Found C, 53.52; H, 8.28; N, 3.61; Cl, 9.52.

EXAMPLE 16

Hexahydro-1-[3-(1-pyrrolidinyl)propyl]-3a, 5, 6, 7a-indantetrol

1-[3-Indenyl)propyl]pyrrolidine

A mixture of 3-(3'-bromopropyl)indene (95 g.; 0.4 mole), freshly distilled pyrrolidine (64 g.; 0.09 mole), and 400 ml. of toluene is refluxed for 2 hours. Upon cooling pyrrolidine hydrobromide separates as oily crystals. The toluene solution is decanted and the remaining hydrobromide salt is extracted with ether. The combined organic fractions are evaporated and the remaining oily product (1-[3-(3-indenyl)propyl]pyrrolidine) is vacuum distilled. A sample is converted into the hydrochloride (m.p. 134°).

Analysis, Calculated for $C_{16}H_{22}NCl$: C, 72.84; H, 8.41; N, 5.31; Cl, 13.44. Found: C, 72.83; H, 8.25; N, 5.19; Cl, 13.66.

1-[3-(4,7-Dihydro-1-indanyl)propyl]pyrrolidine

A solution of 1-[3-(3-indenyl)propyl]pyrrolidine (27 g.; 0.119 mole) in 100 ml. of ether is added to 2 liters of liquid ammonia. Lithium ribbon (40 g.) is added in portions over a period of 30 minutes. Stirring is continued for 2.5 hours, after which absolute ethanol is added over a period of 1.5 hours, until the color is discharged. The ammonia is allowed to evaporate and the residue is diluted with 2.5 l. of water and extracted with ether. After drying over $MgSO_4$ the solvent is evaporated to yield 26 g. of oily product 1-[3-(4,7-dihydro-1-indanyl) propyl]pyrrolidine (94%). U. V. indicated that no aromatic starting material is present. A sample of the diene is converted into the hydrochloride salt (m.p. 157°).

Analysis Calculated for $C_{16}H_{26}ClN$: C, 71.74; H, 9.79; N, 5.23; Cl, 13.24. Found: C, 71.61; H, 9.93; N, 5.19; Cl, 12.13

Hexahydro-1-[3-(1-pyrrolidinyl)propyl]-3a, 5, 6, 7a-indantetrol

To ice cold formic acid (98%; 200 ml.) there is added dropwise over a period of 15 minutes 1-[3-(4,7-dihydro-1-indanyl)propyl]pyrroldine as prepared above (22 g.; 0.095 mole). Upon completion there is added hydrogen peroxide (30%) (115 ml.) at a rate as to maintain 20°, after which the temperature is allowed to rise to 35°. This is followed by stirring at room temperature overnight. The mixture is evaporated and freed of the performic acid by addition of water and evaporation under vacuum. The resulting oil is dissolved in 200 ml. of 95% ethanol and a solution of 60 g. KOH in 100 ml. of water. After refluxing the mixture for one hour water is added until 100 ml. of total volume is reached. Exhaustive ether extraction furnishes an oil which solidifies upon trituration with ethyl acetate. Recrystallization from the same solvent furnishes 7 g. of the above-titled product (m.p. 188°–90°, 31%).

Analysis, Calculated for $C_{16}H_{29}NO_4$: C, 64.18; H, 9.76; N, 4.68. Found: C, 64.09; H, 9.77; N, 4.60.

EXAMPLE 17

3a, 7a-trans-5,6-trans-Hexahydro-1-[3-(1pyrrolidinyl)propyl]-3a, 5,6,7a-indantetrol, 3a, 5,6,7a-tetraacetate Hexahydro-1- [3-(1-pyrrolidinyl)]-3a, 5,6,7a-indantetrol as prepared in Exaple 16 (1.5 g.; 0.0005 mole) is dissolved in a mixture of acetic anhdyride (30 ml.) and acetic acid (0.5 ml.). The solution is chilled in a dry ice/acetone bath and perchloric acid is added dropwise (70%; 3 ml.). The dark mixture is kept overnight at −15°. With external cooling there is added 30 ml. of methanol and concentrated ammonia. The product is exhaustively extracted with chloroform. After drying and evaporation of the solvent there is obtained a brown oil which solidifies on standing. Recrystallization from hexane furnishes 1.07 g. of the above-titled compound (48%) m.p. 146–7°.

Analysis, Calculated for $C_{24}H_{37}NO_8$: C, 61.65; H, 7.98; N, 3.00. Found: C, 61.43; H, 7.99; N, 2.85.

EXAMPLE 18

A mixture of 5 ml. pyridine, 1.5 ml. benzoyl chloride and 0.6 g. 3a, 7a-trans-5,6-trans-hexahydro-1-[3-(1-pyrrolidinyl)propyl]-3a, 5,6,7a-indantetrol as prepared in Example 16 is heated on a steam bath for 1 hour. Excess solvent is evaporated and the residue is treated with saturated sodium bicarbonate solution. The mixture obtained is extracted with chloroform. After drying and evaporation, the residue is chromatographed on neutral alumina (Act IV). Three fractions are obtained. The third fraction is crystallized twice from ether and 3a,7a-trans-5,6-trans-hexahydro-1-[3-(1-pyrrolidinyl)propyl]-3a, 5,6,7a-indantetrol, 5,6-dibenzoate.

Analysis, Calculated: C, 70.98; H, 7.35; N, 2.76. Found: C, 70.80; H, 7.37; N, 2.73

EXAMPLE 19

3a,7a-trans-5,6-trans-Hexahydro-2-(2-piperidinoethyl)-3a, 5,6,7a-indantetrol

2-Indanethanol

To a well stirred suspension of 5 gm. of lithium aluminum hydride in 200 ml. of dry ether, a solution of 17.5 gm. (0.1 mole) of 2-indanylacetic acid in 500 ml. of dry ether is added dropwise over a period of 1½ hrs. The mixture is stirred at room temperature for 2 days. To the cooled mixture, 100 ml. of water is added dropwise followed by 200 ml. of 2N $H_2SO_4$. The ether layer is separated. The aqueous layer is extracted with a second portion of ether. The ethereal extracts are combined, dried ($MgSO_4$) and evaporated in vacuo to give 16 gm. (98%) of 2-indanethanol as an oil; $\lambda_{liq.}^{max.}$ film 3400 cm.$^{-1}$ (O—H).

p-Toluene sulfonic acid, ester with 2-indanethanol (II)

To 16.2 gm. (0.085 mole) of p-toluenesulfonic chloride, 12 gm. (0.074 mole) of 2-indanethanol is added dropwise with stirring. The mixture is cooled in an ice bath and 12 cc. of pyridine is added dropwise over a period of 25 minutes. The mixture is kept in the cold for 4 hrs., acidified, and extracted with 600 ml. of ether. The ether extract is washed with water, dried ($MgSO_4$) and evaporated in vacuo to give 19.4 gm. (84%) of yellowish white solid; melting 59°–65°C. Crystallization from ether gives 18 g. (77%) of p-toluene sulfonic acid, ester with 2-indanethanol as white crystals; m.p. 75.5°–78.5°; $\lambda_{Nujol}^{max.}$ 1420–1330 cm.$^{-1}$, 1200–1145 cm.$^{-1}$ (sulfonate), $\tau CDCl_3$ 8.4 (Ar—$CH_3$), 7.4–9.5

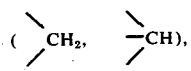

5.7–6.1 ($CH_2$ adjacent to

1.8–3 (aromatic protons).

Analysis, Calculated for: $C_{18}H_{20}O_3S$: C, 68.46; H, 6.54; Found: C, 68.33; H, 6.37.

1-[2-Indanyl)ethyl]piperidine

To a solution of 18 gm. (0.057 mole) of p-toluene sulfonic acid, ester with 2-indanethanol in 100 ml. of toluene, 14 cc. (0.143 mole) of piperidine is added. The mixture is refluxed for 11.5 hrs. and treated with 250 ml. of water and 100 ml. of ether. The organic layer is separated, washed with water, dried ($MgSO_4$) and evaporated in vacuo to give a dark colored oil. The oil is treated with ethereal — HCl to give 15.7 gm. (97%) of 1-[2-(2-indanyl)ethyl]piperidine hydrochloride. Crystallization from ethanol-ether gives 11.5 gm. (72%) of product as off-white crystals; m.p. 204.5°–207°, $\lambda_{Nujol}^{max.}$ 2700–2250 cm$^{-1}$ (—NH+).

Analysis, Calculated for: $C_{16}H_{23}N$ .HCl: C, 72.30; H, 9.10; N, 5.28. Found: C, 72.28; H, 9.22; N, 5.18.

3a,7a-trans-5,6-trans-Hexahydro-2-(2-piperidinoethyl)-3a, 5,6,7a-indantetrol a. Birch Reduction To a mixture of 1 l. of liquid ammonia and 100 ml. of anhydrous ether, a solution of 7.8 gm. (0.03 mole) of 1-[2-(2-indanyl)ethyl] piperidine in 100 ml. of anhydrous ether is added with stirring. To this mixture 12 g. (1.75 mole) of lithium ribbon is added over a period of 15 minutes. The bronze-blue mixture is stirred 1 hr. and 45 minutes. Absolute ethanol (175 ml.) is added dropwise to discharge the blue color. The solvent is allowed to evaporate overnight. The residual material is cooled and diluted to 1500 ml. with water and ice. The aqueous mixture is extracted three times with 400 ml. of ether. The ether extract is dried ($MgSO_4$) and evaporated in vacuo to give 5.2 gm. (66%) of 1-[2-(4,7-dihydro-2-indanyl)ethyl]piperidine as a crude oil; $\lambda_{liq.}^{max.}$ film 1650 cm$^{-1}$.

b. Hydroxylation

To 100 ml. of cold 98% formic acid, 5 gm. (0.02 mole) of 1-[2-(4,7-dihydro-2-indanyl)ethyl]piperidine is added dropwise over a period of 15 minutes. To this mixture 13 gm. (0.12 mole) of 30% $H_2O_2$ is added at such a rate as to maintain a temperature of 20°C. The temperature is then allowed to rise to 30°C. The solution is stirred on a water bath overnight. The reaction mixture is taken to dryness, the addition of water and evaporation in vacuo serving to remove the traces of performic acid. The crude oil is cooled in an ice bath and a solution of 7 gm. of potassium hydroxide in 50 ml. of water is added dropwise at such a rate that the temperature does not exceed 20°C. The mixture is stirred at 45°C. for 0.5 hour. The mixture is extracted with CHCl₃, washed with water, dried (MgSO₄) and evaporated in vacuo to give 2 gm. (30%) of the above entitled compound as a crude white solid, m.p. 136°–145°. Two recrystallizations from ethyl acetate give 0.84 gm. (14%) of product as white crystals; m.p. 174°–175°C., $\lambda_{Nujol}^{max.}$ 3500 cm$^{-1}$ —3400 (O—H).

Analysis. Calcd. for $C_{16}H_{29}NO_4$: C, 64.18; H, 9.76; N, 4.68. Found: C, 64.12; H, 9.65; N, 4.61.

EXAMPLE 20

Hexahydro-2-(2-piperidinoethyl-3a,5,6,7a-indantetrol acetate ester (1:4)

A solution of 3a,7a-trans-5,6-trans-hexahydro-2-(2-piperidinoethyl)-3a,5,6,7a-indantetrol (5 g., 0.016 mole) in 80 ml. of acetic anhydride and 10 ml. glacial acetic acid is cooled in an ice-salt bath and 70% perchloric acid (80 ml.) is added dropwise. The dark solution is kept at −15°C. for 17 hours. The mixture is cooled, methanol (80 ml.) added dropwise and the solution made alkaline with concentrated ammonium hydroxide. The aqueous layer is extracted with chloroform, dried (MgSO₄) and evaporated in vacuo to give 5.3 g. (68%) of crude white solid. Crystallization from ether-pentane gives 3.4 g. (44%) of the above titled product as white crystals; m.p. 155°–157° C.: $\lambda_{Nujol}^{max.}$ 1735 cm.$^{-1}$ (C=O).

Analysis. Calcd. for $C_{24}H_{37}NO_8$: C, 61.65; H, 7.98; N, 3.00. Found: C, 61.90; H, 7.72; N, 3.05.

EXAMPLE 21

3a,7a-trans-5,6-trans-Hexahydro-1-[4-(1-methyl-2-piperidyl)butyl]-3a,5,6,7a-indantetrol 2-[4-(Inden-3-yl)butyl]pyridine Sodium amide is prepared by adding 25 g. of sodium, in several portions, to 1 l. liquid ammonia containing a trace of Fe(NO₃)₃ . 9H₂O . 2-Picoline (186 g., 2.0M) is added over a period of a few minutes and the blood red mixture is stirred 10 minutes. A solution of 3-(3'-bromopropyl)indene (119 g.—0.5 M) in ether is added as rapidly as possible and the resulting dark brown mixture is stirred one hour. Ammonium chloride (125 g.) is added in several portions. Ether (500 ml.) is added to the charcoal gray mixture and the ammonia is boiled off. Solids are removed by filtration and washed with ether. The filtrate is concentrated in vacuo. Distillation of the brown oil yields 57.4 g. (46%) of yellow oil (2-[4-(inden-3-yl)butyl]pyridine) boiling at 154°–156°/0.1 mm.

2-[4-(1-Indanyl)butyl]piperidine

A solution of 50.0 g. (0.2 M) of the pyridine compound described above in 150 ml. of glacial acetic is treated with 1.0 g. platinum oxide and shaken under up to 55 psi of hydrogen while being heated at 40°C. for 5½ hours. No significant uptake is noted during the last 2 hours. After filtering, the acid is removed in vacuo, the residue is dissolved in water, basified and the product extracted with ether. Distillation of the ether extract yields 42.8 g. (82%) of oil (2-[4-(1-indanyl)-butyl]piperidine boiling at 144–146/0.2 mm.

N-Methyl 2-[4-(1-indanyl)butyl]piperidine 42.8 g. (0.166 M) of 2-[4-(1-indanyl)butyl]piperidine prepared above is mixed with 100 ml. of 37% formalin and then treated with 200 ml. of 98% formic acid. The resulting solution is heated overnight on a steam bath. The reaction mixture is worked up by concentrating in vacuo, dissolving in water, basifying, and extracting with ether. The ether extracts are dried over NaOH. Distillation yields 36 g. (80%) of N-methyl-2-[4-(1-indanyl)butyl]piperidine boiling at 149°–152°/0.3 mm.

3a,7a-trans-5,6-trans-Hexahydro-1-[4-(1-methyl-2-piperidyl)butyl]-3a,5,6,7a-indantetrol A solution of the N-methyl-2-[4-(1-indanyl)butyl]-piperidine prepared above (15 g., 0.057 M) in 100 ml. ether is added to 1 l. liquid ammonia and 100 ml. ether. Lithium ribbon (20 g.) is added in several portions over a period of 15 minutes. The bluish-bronze mixture is stirred 75 minutes before absolute ethanol is added dropwise until the color is discharged (400 ml. required added over a period of 2 hours). After the ammonia is evaporated, the residue is diluted to 1500 ml. with water and extracted two times with ether. The ether extracts are dried over potassium carbonate and the solvent is removed in vacuo leaving 15.5 g. (100%) of oil (1-[4-(1-methyl-2-piperidyl)butyl]-4,7-dihydroindane). The UV indicates none of the starting material remains.

The crude diene (0.057 M) described above is added dropwise over a period of 15 minutes to 100 ml. cold 98% formic acid. This is followed by dropwise addition (30 minutes) of 57 g. 30% hydrogen peroxide maintaining a temperature of 20°. The temperature is then allowed to rise to 35° and held at 30°–35°, using a large water bath, for 3 hours. The mixture is then left stirring overnight. The mixture is taken to near dryness and any residual performic acid is removed by twice adding water and removing in vacuo.

The remaining viscous material is dissolved in 100 ml. absolute ethanol and treated with a solution of 30 g. KOH in 50 ml. water. The mixture is heated under reflux 1 hour, cooled and diluted to 500 ml. with water. Three ether extractions yields 10.5 g. (54%) of a brown oil. After 3 months, 1.9 g. (10%) of crystalline tetrol is obtained from an ethyl acetate-ether solution which has been left in a cold room (− °C). This is easily recrystallized from ethyl acetate to give 1.35 g. (7%) of the above titled compound melting at 152°–155°C.

Analysis, calcd. for C, 66.82; H, 10.33; N, 4.10. Found: C, 66.88; H, 10.43; N, 3.88.

EXAMPLE 22

3a,7a-trans-5,6-trans-hexahydro-1-[2-(1-methyl-2-piperidyl)ethyl]-3a,5,6,7a-indantetrol 3-[2-(2-pyridyl)ethyl]indene This compound is prepared as described by Dressler and Kurland J. O. C. 29, 175 (1964). Under nitrogen gas, 500 g. indene plus 5 g. potassium t-butoxide are stirred and heated to 130°. 2-Vinyl pyridine (220 g., 2.0 M) is added dropwise over a period of 1 hour keeping the temperature at 135°–145°C. during addition and for 2 hours after addition is completed. The reaction mixture is cooled and 25 ml. acetic acid is added, followed by filtration. A flash distillation yields 395 g. (84%) crude product boiling 160°–175°/0.3 mm. This is redistilled to give 353 g. (75%) of oil (3-[2-(pyridyl)ethyl]indene) boiling point 135°–140°/0.1 mm.

1-[2-(2-piperidyl)ethyl]indane

A solution of 44.2 g. (0.20 M) of the pyridine compound described above in 150 ml. glacial acetic acid is treated with 1.0 g. platinum oxide and shaken under up to 55 psi of H₂ while being heated at 50°. The reduction is apparently complete after 7½ hours and yields 45 g. (about 100%) of 1-[2-(2-piperidyl)ethyl]indane.

N-methyl-1-[2-(2-piperidyl)ethyl]indane 45 g. of 1-[2-(2-piperidyl)ethyl]indane prepared as described above is mixed with 100 ml. of 37% formalin and 200 ml. of 98% formic acid is added while swirling and the solution is then heated overnight on a steam bath. The reaction mixture is worked up by concentrating in vacuo, dissolving in water, filtering, basification and extraction with ether. The ether extracts are dried over potassium hydroxide and after removal of the ether, the product is distilled collecting 42.6 g. (88%), N-methyl-1-[2-(2-piperidyl)ethyl]indane, boiling point 128°–130°C/0.2 mm.

3a,7a-trans-5,6-trans-Hexahydro-1-[2-(1-methyl-2-piperidyl)ethyl]-3a,5,6,7a-indantetrol A solution of 15.0 g. (0.06 M) of the N-methyl-1-[2-(2-piperidyl)ethyl]indane described above in 100 ml. ether is added to 1 l. liquid ammonia and 100 ml. ether. While stirring 20 g. lithium ribbon is added in several portions over a period of 15 minutes. After 45 minutes absolute ethanol is added dropwise until the blue color is discharged (400 ml. required added over a period of 2½ hours). The ammonia is evaporated and the residue is diluted to 1500 ml. with water and extracted two times with ether. The ether extracts are dried over potassium carbonate and the ether is removed in vacuo leaving 15.6 g. of oil (1-[2-(1-methyl-2-piperidyl)ethyl]-4,7-dihydro indane). The UV of this material indicates about 10% of aromatic material remains.

The crude diene described above is added dropwise over a period of 15 minutes to 100 ml. cold 98% formic acid. This is followed by dropwise addition (30 minutes) of 57 g. (about .5M) of 30% hydrogen peroxide maintaining a temperature of 20°. The temperature is then allowed to rise to 35° and is held at 30°–35°, using a large water bath, for 3 hours. It is then left stirring overnight. The reaction mixture is taken to near dryness and any residual performic acid is removed by twice adding water and removing in vacuo.

The remaining viscous yellow material is dissolved in 100 ml. absolute ethanol and a solution of 30 g. potassium hydroxide in 50 ml. water is added. After heating under reflux for 1 hour the dark brown solution is diluted to 500 ml. with water. Three ether extracts yield 10.5 g. (about 56%). An ethyl acetate-ether solution of the material is left in a cold room (0 °C.) and after 2 months, 1.5 g. of crystalline material is deposited. This is recrystallized from ethyl acetate yielding 1.1 g. (5.9%) of the above entitled compound melting at 143°–153°C.

Analysis, Calcd. for $C_{17}H_3NO_4$: C, 65.14; H, 9.97; N, 4.47. Found: C, 65.09; H, 9.90; N, 4.28.

EXAMPLE 23

1-[1-(Dimethylamino)]-3-propyl-indene

A rapidly stirred mixture of 300 g. of sodium hydroxide, 300 ml. of water and 30 ml. of 40% Triton B in methanol is heated to 50°. A mixture of 232 g. (2.0 moles) of indene and the free base (about 164 g.) prepared from 264 g. (1.6 mole) of $(CH_3)_2N(CH_2)_3Cl$; HCl is added in portions over 60 minutes to maintain the temperature between 50° and 60°. The resulting green mixture is stirred at 60° for 4 hours, cooled, diluted with 1.5 l. of water and extracted with ether (3 × 400 ml.). The ether extract is washed with a mixture of 180 ml. of concentrated hydrochloric acid and 600 ml. of water. The aqueous phase is separated, basified with 100 g. of sodium hydroxide in 300 ml. of water and washed with ether (3 × 300 ml.). The ether extract is washed with water, saturated salt solution and dried. Solvent removal gives 182 g. of brown oil. Distillation gives, after a low boiling forerun, 102 g. of 1-[1-(dimethylamino)]-3-propyl-indene, b.p. 88°–93°C. 0.05 mm.

EXAMPLE 24

1-(1-Indanyl)piperidine

A mixture of 100 g. of 1-indanone (0.758 mole) and 125 ml. of piperidine in 750 ml. of toluene is treated with 0.5 g. of p-toluenesulfonic acid and heated under reflux with a water take-off trap attached. Heating is continued for 48 hours. Solvent and excess piperidine are removed in vacuo and the residue is dissolved in 1500 ml. of absolute methanol. The resulting solution is stirred and treated portionwise with 50 g. of sodium borohydride below 30°C. After stirring several hours longer, the mixture is treated with a small amount of acetic acid then made strongly basic by the addition of sodium hydroxide solution. After 400 ml. of water is added, most of the methanol is removed in vacuo. Product is extracted into ether, dried over potassium hydroxide and distilled. 119.7 g. of 1-(1-indanyl)piperidine is collected at 101°–102° (0.2 mm.).

EXAMPLE 25

1-(1-Tetrahydronaphthyl)piperidine a. 1-Piperidino-3,4-dihydronaphthalene

A solution of 146 g. (1.00 mole) of 1-tetralone and 150 ml. of piperidine in 1 l. of toluene is treated with 1 g. of p-toluenesulfonic acid and heated for 11 days under reflux with a water take-off trap attached. 13.1 ml. of water is collected. Fractional distillation affords 105.3 g. of 1-piperidino-3,4-dihydronaphthalene collected at 118°–120° (0.2 mm.).

b. 1-(1-Tetrahydronaphthyl)piperidine

An ether solution of 48 g. of 1-piperidino-3,4-dihydronaphthalene as prepared above is treated with gaseous HCl to precipitate the salt. Rapid filtering to avoid hydrolysis by moisture followed by drying over potassium hydroxide in a vacuum dessicator provides a white powder salt which is added portionwise to an ether suspension of excess lithium aluminum hydride. After 1 hour of stirring, the excess reagent is decomposed by the cautious dropwise addition of potassium carbonate solution until a granular white precipitate forms. Filtration and concentration leaves an oil which is fractionally distilled to yield 25 g. of 1-(1-tetrahydronaphthyl)piperidine collected at 102°–106° (0.3 mm.).

EXAMPLE 26

3a-7a-trans-5,6-trans-1-[3-(Dimethylamino)propyl]-hexahydro-3a,5,6,7a-indantetrol a. N,N-Dimethylinden-3-propylamine The general procedure of Makosza (M. Makosza, *Tet. Letters*, (38) 4621 (1966) is employed to prepare N,N-dimethylinden-3-propylamine.

A mixture of 232 g. (2.0 moles) of indene and the free base prepared from 264 g. (1.6 moles) of 3-dimethylaminopropylchloride-hydrochloride is added in portions over 1 hour to a rapidly stirred mixture of 300 g. (7.5 moles) of sodium hydroxide, 300 g. of water and 300 ml. of 40% Triton B in methanol. The initial temperature is 50° and the rate of addition controlled to keep the temperature between 55°–60°. The green mixture is stirred at 60° for 4 hours, cooled, diluted with 1500 ml. of water and extracted with ether. The ether extract is in turn extracted with a solution of 180 ml. of conc. hydrochloric acid in 600 ml. of water and the aqueous phase separated, basified with 100 g. of sodium hydroxide and extracted with ether. Solvent removal gives 182 g. of brown oil which is distilled to give 102 g. of oil, b.p. 88°–93° at 0.05 mm. Redistillation gives 19.6 g.; b.p. 87.5°–89.5° at 0.05 mm. and 71.1 g.; b.p. 89.5°–90° at 0.05 mm.

b. 4,7-Dihydro-N,N-dimethyl-1-indanpropylamine

A solution of 35 g. (0.174 mole) of N,N-dimethylinden-3-propylamine in a total volume of 125 ml. of ether is added to 2 liters of liquid ammonia. Over 1 hr., 44 g. (6.3 g-atoms) of lithium ribbon is added at the reflux temperature. After a total of 3 hours, the reaction mixture is blue. 550 ml. of ethanol is added over 135 min. whereupon the blue color fades. The ammonia is allowed to evaporate overnight and the residue dissolved in 1500 ml. of water and extracted twice with ether. The ether extract gives 34.5 g. (98.6%) of crude diene upon drying and solvent removal which contains ca, 10% of the corresponding aromatic compound by nmr integration.

c. 3a,7a-trans-5,6-trans-1-[3-(Dimethylamino)propyl]-hexahydro-3a,5,6,7a-indantetrol A solution of 34.5 g. (0.172 mole) of 4,7-dihydro-N,N-dimethyl-1-indanpropylamine in 300 ml. of formic acid is prepared by dropwise addition of the diene to formic acid cooled in an ice bath. The temperature of the bath is raised to 15° and 150 ml. of 30% hydrogen peroxide (ca. 1.5 moles) is added over 1 hr. keeping the temperature below 20°. The temperature of the bath is raised to 30° for 1 hour and then the mixture is stirred at ambient temperature overnight. Water (200 ml.) is added and ca. 300 ml. of solvent is distilled in vacuo. This process is repeated until 1400 ml. of solvent is collected and then the solvent is totally removed to give an oil which is refluxed with 80 g. of potassium hydroxide in a mixture of 300 ml. of ethanol and 150 ml. of water for 1 hr. The mixture is cooled, diluted with 200 ml. of water and the solvent reduced in volume to 300 ml. This process is repeated three times. The final volume is adjusted to 700 ml. with water and the solution is extracted with ether and chloroform (8 × 150 ml.). The chloroform extract gives 14.6 g. of oil which solidifies on trituration with 60 ml. of ethyl acetate. The solvent is decanted and the solid recrystallizes three times from ethyl acetate to give 3.71 g., m.p. 136°–138°.

Anal. Calc'd for $C_{14}H_{27}NO_4$: C, 61.51; H, 9.96; N, 5.12. Found: C, 61.50; H, 9.84; N, 5.09.

EXAMPLE 27

3a,7a-trans-5,6-trans-1-[3-(Dimethylamino)propyl]-hexahydro-3a,5,6,7a-indantetrol, acetate ester (1:4)

A well-powdered, 3.6 g. (0.0132 mole) sample of 3a,7a-trans-5,6-trans-1-[3-(dimethylamino)propyl]-hexahydro-3a,5,6,7a-indantetrol prepared as in Example 26 is stirred with 60 ml. of acetic anhydride and 2 ml. of acetic acid until solution occurs. The solution is cooled in a dry ice-acetone bath and 4.5 ml. of 70% perchloric acid is added. The mixture is stored overnight at −15°, cooled in an ice-acetone bath and 35 ml. of methanol added over 30 min. (internal temperature less than −10°). The resulting solution is poured into a cold mixture of 100 ml. of conc. ammonium hydroxide and 200 ml. of ether. The ether solution is separated, washed with water, saturated salt solution, dried and evaporated to give 5.6 g. (95%) of crude solid. Two recrystallizations from hexane/ethyl acetate gives 3.21 g., m.p. 169°–170.5°.

Anal. Calc'd for $C_{22}H_{35}NO_8$: C, 59.84; H, 7.99; N, 3.17. Found: C, 59.59; H, 8.22; N, 3.09.

EXAMPLE 28

3a,7a-trans-5,6-trans-Hexahydro-1-(3-aminopropyl)-3a,5,6,7a-indantetrol a. 4,7-Dihydro-1-indanpropylamine, hydrochloride To 14.6 g. lithium aluminum hydride in 1 liter anhydrous ether under nitrogen is added 61.4 g. (0.379 mole) indene-3-propionitrile in 500 ml. anhydrous ether slowly with stirring. After stirring overnight under nitrogen, 14.6 ml. water 14.6 ml. 15% sodium hydroxide solution, and 43.8 ml. water are added slowly with stirring. The precipitate is filtered and washed with ether. Evaporation of the ether yields 61.4 g. (95%) indene-3-propylamine.

To a solution of 61.4 g. (0.356 mole) of the above propylamine and 175 ml. anhydrous ether in 2 liters liquid ammonia is added 29.4 g. lithium ribbon over 1 hour. After stirring for 1 hour, 340 ml. absolute ethanol is added over 2.5 hours until the solution turns white. The ammonia is allowed to evaporate overnight. The solid is dissolved in 1 liter of water and extracted with ether. The organic layer is dried twice (sodium sulfate) and evaporated to yield 62 g. (92%) 4,7-dihydro-1-indanpropylamine.

To 15 g. of the preceding compound in 70 ml. 2-propanol is added hydrochloric acid in 2-propanol until the solution is acidic to pH paper. Ether is added and the precipitate filtered to afford a quantitative yield (18 g.) of crude 4,7-dihydro-1-indanpropylamine, hydrochloride.

Recrystallization of 5 g. of the above hydrochloride from 2-propanol and ether affords the above-titled compound, 1.1 g., m.p. 114°–115°C.

Anal. Calc'd for $C_{12}H_{20}NCl$: C, 67.43; H, 9.43; N, 6.56; Cl, 16.59. Found: C, 67.27; H, 9.64; N, 6.47; Cl, 16.37.

b. N-[3-(4,7-Dihydro-1-indanyl)propyl]-2,2,2-trifluoroacetamide

To a solution of 15 g. (.085 mole) 4,7-dihydro-1-indanpropylamine (free base) in 255 ml. anhydrous ether is added 58.3 g. sodium carbonate with stirring. The mixture is cooled and 100 g. (0.477 mole) trifluoroacetic anhydride is added over 1.5 hours with stirring. The ice bath is removed and the mixture stirred vigorously for 30 minutes. The entire mixture is poured into 400 ml. CHCl₃ and ice added. The mixture is shaken with water for 20 minutes. The organic layer is removed, dried over sodium sulfate, and on evaporation affords a quantitative yield of crude N-[3-(4,7-dihydro-1-indanyl)propyl]-2,2,2-trifluoroacetamide.

A 5 g. sample of trifluoroacetamide is recrystallized from warm hexane to afford 1.6 g. of the above-titled compound (b), m.p. 61°–62° C.

Anal. Calc'd for $C_{14}H_{18}NOF_3$: C, 61.53; H, 6.64; N, 5.12; F, 20.86. Found: C, 61.29; H, 6.64; N, 5.05 F, 20.60.

c. 3a,7a-trans-5,6-trans-Hexahydro-1-(3-aminopropyl)-3a,5,6,7a-indantetrol

The N-[3-(4,7-dihydro-1-indan)propyl]-2,2,2-trifluoroacetamide can be converted to the above-titled indantetrol employing a procedure similar to that employed in Example 2.

EXAMPLE 29

3a,7a-trans-5,6-trans-Hexahydro-1-(3-(benzamido)-propyl)-3a,5,6,7a-indantetrol a. N-[3-(4,7-Dihydro-1-indanyl)propyl]benzamide To a solution of 7 g. (.0396 mole) of 4,7-dihydro-1-indanpropylamine (free base) in 100 ml. pyridine at 0° C., is added 10 ml. benzoyl chloride with stirring over 15 minutes. The solution is kept at 0° C. overnight. Ice and water are added (about 400 ml.) and the precipitated solid filtered and washed with water. This solid is dissolved in dichloromethane and washed with 10% sulfuric acid and water. The organic layer is dried (sodium sulfate) and evaporated to yield 9.5 g. (85%) N-[3-(4,7-dihydro-1-indanyl)propyl]benzamide.

A 2.6 g. sample of the benzamide is recrystallized twice from dichloromethane and hexane to afford 1.4 g. of analytical sample, m.p. 112.5°–113.5° C.

Anal. Calc'd for $C_{19}H_{23}NO$: C, 81.10; H, 8.24; N, 4.98 Found: C, 81.05; H, 8.14; N, 5.20.

b. 3a,7a-trans-5,6-trans-Hexahydro-1-(3-(benzamido)-propyl)-3a,5,6,7a-indantetrol The N-[3-(4,7-dihydro-1-indanyl)propyl]benzamide can be converted to the above-titled indantetrol employing a procedure similar to that described in Example 2.

EXAMPLE 29a 5,6-trans-4,5,6,7-Tetrahydro-2-piperidino-5,6-indandiol

A solution of 50.5 g. (0.25 mole) of 4,7-dihydro-1-indanyl piperidine in 1 liter of dry acetic acid (fresh bottle) is prepared and treated with 83.5 g. (0.50 mole) of dry silver acetate under $N_2$. The stirred suspension is then treated portionwise with 62.75 g. (0.25 mole) $I_2$ over one-half hr. The stirred mixture is then heated to 90°–95° for 3 hours, cooled, filtered and taken to dryness. The residue, which is identified as 5,6-trans-4,5,6,7-tetrahydro-2-piperidino-5,6-indandiol diacetate, is dissolved in 250 ml. methanol and treated with 50 ml. 50% NaOH with stirring. After stirring overnight, the solution is diluted with water and the product extracted into $CHCl_3$. After drying and solvent removal, the crude product is taken up in hot isopropyl alcohol and the solution rendered turbid with ether. A 25 g. first crop is obtained. Further crops of 12 g. are obtained on rework. Total crude yield is 37g. (63%), m.p. 149°–167°. IR indicates the absence of the cis isomer. Recrystallization of 6.0 g. of first crop material twice from benzene provides 2.8 g. of pure material 156°–157.5°.

Anal. Calcd. for $C_{14}H_{23}NO_2$: C, 70.85; H, 9.77; N, 5.90. Found: C, 70.66; H, 9.75; N, 5.94.

The indandiol can be converted to the corresponding tetrol, 3a,7a-trans-5,6,-trans-hexahydro-1-piperidino-3a,5,6,7a-indantetrol (Type A), by reacting the indandiol with formic acid and hydrogen peroxide and subjecting the product to basic hydrolysis as outlined in Example 2.

EXAMPLE 30

3a,7a-trans-5a,6-trans-Hexahydro-2-piperidino-3a,5,6,7a-indantetrol (Type B)

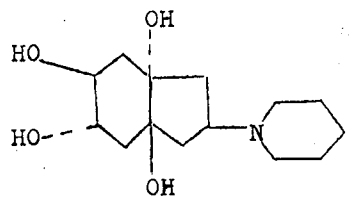

trans        trans (diequatonal)  (diaxial)

The above titled compound is prepared from 5,6-trans-4,5,6,7-tetrahydro-2-piperidino-5,6-indandiol diacetate by reacting the diacetate with formic acid and hydrogen peroxide and then subjecting the product to basic hydrolysis as outlined in Example 2.

EXAMPLE 31

5,6-cis-4,5,6,7-Tetrahydro-2-piperidino-5,6-indandiol

A solution of 10.1 g (0.05 mole) of 4,7-dihydro-1-indanyl-piperidine in 250 ml. acetic acid is prepared and treated with 5 ml. $H_2O$, then covered with a blanket of $N_2$ and treated with 16.7 g. (0.10 mole) of silver acetate. With vigorous stirring, the mixture is treated portionwise with 12.55 g. (0.05 mole) of iodine. The mixture is then heated at 90° for 3 hours under $N_2$. After cooling to room temperature, silver iodide is filtered off and washed with acetic acid. The combined filtrates are freed of solvent and the residue, which is identified as 5,6-cis-4,5,6,7-tetrahydro-2-piperidino-5,6-indandiol-6-monoacetate, is taken up in 100 ml. methanol and treated with 25 ml. 50% NaOH. After stirring overnight, the solution is diluted with water and the product extracted into $CHCl_3$. After drying and solvent removal, the product crystallizes on standing. There is obtained 8.5 g., m.p. 162°–166°, after previous softening. Recrystallization of 5.0 g. twice from benzene provides 2.5 g of analytical material which shrinks at 142° and melts at 156°–168°.

Anal. Calcd. for $C_{14}H_{23}NO_2$: C, 70.85; H, 9.77; N, 5.90. Found: C, 70.94; H, 10.04; N, 5.81.

EXAMPLE 32

3a,7a-trans-5,6-cis-Hexahydro-1-piperidino-3a,5,6,7a-indantetrol (Type C)

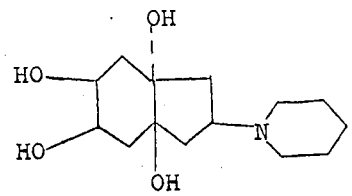

cis        trans (equatonal-axial)  (diaxial)

The above-titled compound is prepared from the indandiol of Example 31 or the diacetate thereof, by reacting the indandiol or diacetate with formic acid and hydrogen peroxide and then subjecting the product to basic hydrolysis as in Example 2.

EXAMPLE 33

3a,7a-cis-5,6-trans-Hexahydro-2-piperidino-3a,5,6,7a-indantetrol (Type D)

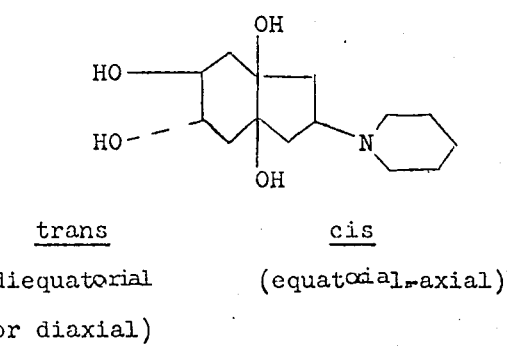

trans      cis (diequatorial    (equatorial-axial)

or diaxial)

The above-titled compound is prepared by dissolving 3.21 g. (0.01 mole) of 5,6-trans-4,5,6,7-tetrahydro-2-piperidino-5,6-indandiol diacetate (as prepared in Example 29a) in a 100 ml. mixture of 75 % benzene and 25 % pyridine. The solution is treated with 1.40 g. (0.01 mole) of osmium tetroxide, and the mixture is stored at room temperature for 3–4 days. The mixture is then cooled to 5°–10°C. and saturated with $H_2S$ gas, whereby a precipitate forms. The mixture is filtered, the precipitate washed with benzene and the filtrates washed with water and dried, and taken to dryness. The resulting residue is purified by crystallization to give 3.1 g, of 3a,7a-cis-5,6-trans-hexahydro-2-piperidino-3a,5,6,7a-indantetrol 3a,7a-diacetate.

The diacetate is hydrolyzed by treatment with ethanol and potassium hydroxide, as described in Example 2, to form the above-titled compound.

EXAMPLE 34

3a,7a-cis-5,6-cis-Hexahydro-2-piperidino-3a,5,6,7a-indantetrol (Type E)

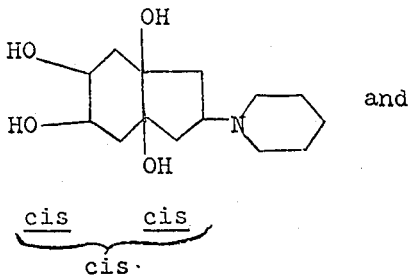 and

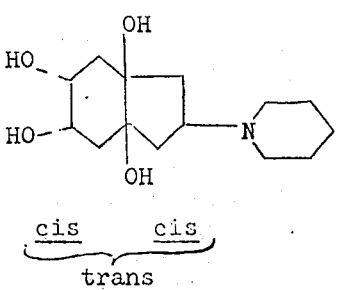

A mixture of the above-described isomers is prepaed by dissolving 2.79 g. (0.01 mole) of 5,6-cis-4,5,6,7-tetrahydro-2-piperidino-5,6-indandiol-6-monoacetate (as prepared in Example 31) in 25 ml. pyridine. The solution is treated with 5 g. (0.05 mole) of acetic anhydride at a temperature of 5°–10°C. After standing for several hours at room temperature, the mixture is poured int 200 ml. of water. 5,6-cis-4,5,6,7-Tetrahydro-2-piperidino-5,6-indandiol-5,6-diacetate is then isolated by extracting the mixture with chloroform and by crystallization of the residue left after removal of solvent.

The above diacetate (3.2 g., 0.01 mole) is then dissolved in a 100 ml. mixture of 75% benzene and 25% pyridine. The solution is then treated with 1.40 g. (0.01 mole) osmium tetroxide, and the mixture is stored at room temperature for several days. The mixture is then cooled to 5°–10°C. and saturated with $H_2S$ gas, whereby a precipitate forms. The mixture is filtered, the precipitate washed with benzene and the filtrates washed with water and dried. The resulting residue after solvent removal is purified by crystallization to give 3.0 g. of 3a,7a-cis-5,6-cis-hexahydro-2-piperidino-3a,5,6,7a-indantetrol-5,6-diacetate, i.e. a mixture of

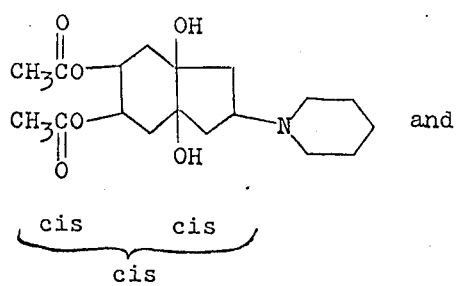 and

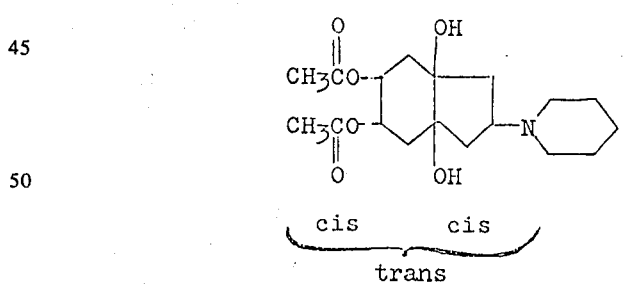

The diacetate diols are converted to the above-described tetrols by hydrolysis by treatment with methanol and potassium hydroxide as described in Example 2.

EXAMPLE 35

3a,7a-trans-1-[3-(Dimethylamino)propyl]-3a,4,7,7a-tetrahydro-3a,7a-indandiol 13.0 g. (0.065 mole) of 1-[3-(dimethylamino)propyl]-4,7-dihydro indane is dissolved in 130 ml. of 93% formic acid at less than 5°. The internal temperature is raised to 23° and 8.0 ml. (ca. 0.078 mole) of 30% hydrogen peroxide is added over 15 min. After a further 15 min., the internal temperature rises to 28° and the mixture is heated to 35° for 2 hours and then the formic acid removed in vacuo. The residue is refluxed with 100 ml. of ethanol, 30 ml. of water and 20 g. of sodium hydroxide under nitrogen for 1 hour, cooled and the mixture diluted with 300 ml. of water and extracted with ether (6 × 200 ml.). The ether extract is dried and evaporated to give 11.8 g. of oil which partially solidifies on trituration with hexane/ether. Filtration gives 1.01 g. of tan solid with one major spot on TLC. The mother liquor is applied to a dry packed, 400 g. column of alumina (3% $H_2O$) and eluted with hexane/chloroform mixtures. A total of 2.2 g. of oil is obtained which shows the same major spot as the above solid. Crystallization from ether gives a total of 1.1 g. of crystalline material which is combined with the 1.01 g. obtained previously and recrystallized twice from ether to give 1.14 g., m.p., 99.5°–101.5°, which is homogeneous on TLC.

Anal. Calcd. for $C_{14}H_{25}NO_2$: C, 70.25; H, 10.53; N, 5.85. Found: C, 70.37; H, 10.56; N, 5.65.

The above indandiol can be converted to the corresponding tetrol {3a,7a-trans-5,6-trans-hexahydro-1-[3-(dimethylamino)propyl]-3a,5,6,7a-indantetrol (Type A)} by reacting the indandiol with formic acid and hydrogen peroxide and subjecting the product to basic hydrolysis as outlined in Example 2.

EXAMPLE 36

3a,7a-trans-3a,4,7,7a-Tetrahydro-2-piperidino-3a,7a-indandiol

A solution of 30.5 g. of 4,7-dihydro-1-indanyl piperidine (free base) (0.15 m.) in 250 ml. 98% formic acid is prepared in the cold and treated dropwise with 18.0 g. of 30% $H_2O_2$ during 10 min. at about 6°C. After stirring in an ice bath for several hours, the mixture is left overnight at room temperature. The mixture is then taken to dryness in vacuum and the residue taken up in 250 ml. ethyl alcohol. The solution is stirred and treated with 50 ml. 50% NaOH. The temperature rises to 65°. The solution is stirred one-half hour longer, diluted with water and extracted 3 times with ether. The extracts are dried ($K_2CO_3$), freed of solvent, treated with hexane and restripped twice. Filtration of the crystalline product affords 30 g. (84%) m.p. 106°–121°.

The above indandiol can be converted to the corresponding tetrol [3a,7a-trans-5,6-trans-hexahydro-2-piperidino-3a,5,6,7a-indantetrol (Type A)] by reacting the indandiol with formic acid and hydrogen peroxide and subjecting the product to basic hydrolysis as outlined in Example 2.

EXAMPLE 37

3a,7a-trans-5,6-trans-1-[3-(Benzylmethylamino)-propyl]-hexahydro-3a,5,6,7a-indantetrol a. n-Butyl 3-(3-indenyl)propionate To a mixture of 4–5 g. of solid potassium t-butoxide in 464 g. (4.0 mole) of indene heated to 120° is added dropwise over 1½ hours 256 g. (2.0 mole) of n-butyl acrylate at 100°–120°. After 1 hour longer at 120°–150°, the mixture is cooled, treated with 25 ml. acetic acid and filtered. Distillation affords 256 g. (57%) of product collected at 143°–160° (2 mm. torr.).

b. 3-(3-indenyl)propanol

A solution of 256 g. (1.06 mole) of the above ester in 1 l. ether is added to a suspension of 80 g. lithium aluminum hydride in 2 l. ether dropwise. After several hours under reflux, the mixture decomposes, is treated with a solution of $K_2CO_3$, and the resulting precipitated solids are filtered off. The filtrates are distilled to yield 155 g. (84%) of 3-(3-indenyl)propanol collected at 125°–130° (1.0 mm. torr.).

c. 4,7-Dihydro-3-(3-indenyl)propanol

A solution of 76.3 g. (0.434 mole) of the above alcohol in 1500 ml. liquid $NH_3$ plus 500 ml. ether is treated portionwise with 40 g. lithium ribbon cut in small pieces. After one-half hour, the mixture is treated dropwise with absolute ethanol until the color disappears. After removal of $NH_3$ and addition of more ether, the mixture is cooled in ice and treated with water. The layers are separated, the aqueous layer reextracted, and the combined organics dried and distilled. There is obtained 75.7 g. (98%) collected at 103°–108° (0.2 mm./torr).

d. 4,7-Dihydro-3-(3-indenyl)propyl tosylate

A solution of 75.7 g. (0.425 mole) of the dihydroalcohol in 200 ml. pyridine is cooled to −10° to −5° and treated dropwise with a solution of 110 g. (0.58 mole) p-toluenesulphonyl chloride in 400 ml. pyridine. Stirring at 0° is continued for 3 hours longer, and then the mixture is left overnight at 5°–10° (coldroom). The still cold mixture is poured into sufficient dilute HCl-ice to neutralize the pyridine. After brief stirring, the product is extracted into ether, dried over $Na_2SO_4$ and freed of solvent, ultimately at the pump. There remains 133 g. (94%) crude tosylate whose IR. indicates complete conversion.

e. Benzyl-[4,7-dihydro-3-(3-indenyl)propyl]methylamine

A mixture of 100 g. (0.33 mole) crude tosylate and 100 g. (0.80 mole) of methylbenzylamine in 500 ml. toluene is heated under reflux overnight. After cooling and filtration, solvent is removed in vacuum, the residual liquid taken up in ether and refiltered, and excess reagents removed ultimately on the pump in boiling water. There remains 79.5 g. (81%) of crude product.

f. 3a,7a-trans-5,6-trans-1-[3-(Benzylmethylamino)-propyl]-hexahydro-3a,5,6,7a-indantetrol The above crude diene is added to 500 ml. of cold 98% formic acid gradually with stirring. Then 100 ml. (1.0 mole) of 30% $H_2O_2$ is added dropwise at 15°–20°. After 1 hour, the temperature is allowed to rise to 30° and 100 ml. $H_2O_2$ added dropwise. After stirring overnight, the mixture is freed of solvent and excess reagents at about 5 mm. and up to 50°. Water is added and removed similarly 3 times. The residue is dissolved in 250 ml. ethanol and treated with 100 ml. 50% sodium hydroxide portionwise with swirling. The mixture is heated under reflux for 1 hour, cooled, and diluted with 3 volumes of water. Ether extraction yields 37 g. of crude product; chloroform, 2 g. more. (Total 39% crude). Crystallization is induced with a small sample obtained by chromatography on Alumina IV basic and elution with 2–5% methanol in $CHCl_3$. There is thus obtained a first crop of 19 g. (19%). Recrystallization of 5.1 g. of this material from ethyl acetate affords 3.6 g. (13% overall) of analytical material, m.p. 129°–137°.

| $C_{20}H_{31}NO_4$ | Calc. | Found |
|---|---|---|
| C | 68.74 | 68.79 |
| H | 8.94 | 9.05 |

| $C_{20}H_{31}NO_4$ | Calc. | Found |
|---|---|---|
| N | 4.01 | 3.99 |

EXAMPLE 38

3a,7a-trans-5,6-trans-Hexahydro-1-[3-methylamino)-propyl]-3a,5,6,7a-indantetrol

A solution of 7.0 g. 3a,7a-trans-5,6-trans-1-[3-(benzylmethylamino)propyl]-hexahydro-3a,5,6,7a-indantetrol as prepared in Example 37 in 150 ml. ethanol is treated with 1.0 g. Pd on SrCO₃ (Engelhardt) and hydrogenated at up to 50 psi H₂ pressure. Toward the end of the uptake, some heat is applied ($t = 30°-40°$) to hasten complete uptake. Uptake is 20.5 lb. in 344 minutes. After removal of catalyst and solvent, the 5.0 g. (96%) of crude product remaining is recrystallized twice from acetonitrile to yield 3.75 g. (72%), m.p. 128°–133°.

| $C_{13}H_{25}NO_4$ | Calc. | Found |
|---|---|---|
| C | 60.20 | 60.29 |
| H | 9.72 | 10.00 |
| N | 5.40 | 5.65 |

EXAMPLE 39

2-Piperidinomethyl decalenetetrol

A solution of 24.3 g. (0.10m) of 2-piperidino methyl-1-tetralone in 100 ml. ether is added dropwise to a suspension of 5 g. of LiAlH₄ in 250 ml. ether. After stirring 1 hour, the mixture is decomposed with K₂CO₃ solution and filtered, Evaporation of the filtrates leaves 24.1 g. of 1-hydroxy-2-piperidinomethyl tetralin.

The crude product is taken up in 100 ml ether and added to 500 ml of NH₃ (liq) with stirring. The resulting solution is treated portionwise with 14 g. of lithium. After stirring for 1 hour, the mixture is treated slowly dropwise with absolute ethanol until the color discharges completely. After rmoval of NH₃, the residue is cooled, treated with water and extracted several times with ether. The dried extracts are freed of solvent, leaving a quantitative crude yield of 1,2,3,4,5,8-hexahydro-2-piperidino methyl naphthalene.

[This is converted to the above titled tetrol by reaction with H₂O₂-formic acid as described in Example 19].

EXAMPLE 40

1-Diethylaminopropyl-decalenetetrol

To th Grignard reagent prepared from 29 g. (0.20 mole) of diethylaminopropyl chloride and 5.2 g. of magnesium in 200 ml. of tetrahydrofuran is added a solution of 14.6 g. (0.10 mole) of 1-indanone in 100 ml. of tetrahydrofuran. After refluxing for 3 hours, the mixture is decomposed with NH₄Cl solution and the product isolated from the organic solvent by distillation.

The crude diethylaminopropyl tetrahydronaphthol is dissolved in 100 ml. ether and added to 500 ml. of liq. NH₃. The solution is treated with 15 g. of lithium in portions. After one-half hour, the mixture is treated slowly dropwise with absolute ethanol until the color discharges completely. After removal of NH₃, the residue is cooled, treated with water and extracted with ether. The dried extracts are freed of solvent leaving crude 1,2,3,4,5,8-hexahydro-1-diethylaminopropyl-naphthalene which is converted to the above titled as described in Example 26.

EXAMPLE 41

1-N-benzamidopropyl-decalenetetrol

A vigorously stirred mixture of 14.6 g. (0.1 mole) of 1-tetralone and 41.0 g. (0.1 mole) of cyanopropyl-triphenyl phosphonium bromide in 500 ml. of dimethoxyethane under N₂ is treated portionwise with 0.11 mole of 50% NaH dispersed in mineral oil. After stirring under reflux for several hours, the mixture is freed of solvent and the product extracted into ether. The solution of 1-[3-cyanopropylidene]tetralin is then added to a suspension of 10 g. of lithium aluminum hydride in 250 ml. ether, and stirred under reflux for several hours. The mixture is decomposed with K₂CO₃ solution and the organic filtrate taken to dryness. Distillation of the residue yields 1,3-aminopropylidenetetralin collected at about 135–140 (1.0 mm).

This is taken up in 100 ml. ether and added to 500 ml. liq. NH₃. To the solution is added 16 g. of lithium in small portions. After one-half hour stirring, the mixture is treated slowly dropwise with absolute ethanol until the color discharges completely. After NH₃ has evaporated, the mixture is cooled, treated with water and the product extracted into ether and dried (K₂CO₃). Removal of solvent leaves 1,2,3,4,5,8-hexahydro-1-aminobutylnaphthalene which is converted to its N-benzoyl derivative and this to the tetrol as described in Example 29.

EXAMPLE 42

To the Grignard reagent prepared from 29.9 g. (0.20 mole) of diethylaminopropyl chloride and 5.2 g. of magnesium in 250 ml. of tetrahydrofuran is added a solution of 17.4 g. (0.1 mole) of 9-methyl-6,7,8,9-tetrahydro-5H-benzocyclohepten-5-one in 125 ml. of tetrahydrofuran. After 4 hours at reflux, the mixture is decomposed with NH₄Cl solution and the product isolated from the organic solvent.

The crude 5-hydroxy-5-diethylaminopropyl-9-methyl-6,7,8,9-tetrahydro-5H-benzocycloheptene is dissolved in 100 ml. of diethyl ether and added to 500 ml. of liquid ammonia. The solution is treated with 20 g. of lithium is small portions. After one-half hr., the mixture is treated slowly dropwise with absolute ethanol until the color discharges completely. After removal of NH₃, the residue is cooled, treated with water and extracted with ether. The dried extracts are freed of solvent leaving crude 5-diethylaminopropyl-9-methyl-1,4,6,7,-8,9-hexahydro-5H-benzocycloheptene, which is converted to the corresponding tetrol as described hereinbefore.

EXAMPLE 43

A solution of 16.1 g. (0.10 mole) of 6-amino-6,7,8,9-tetrahydro-5H-benzocycloheptene in 100 ml. of diethyl ether and 500 ml. of liquid NH₃ is treated portionwise with 15 g. of lithium in small pieces. After 10 minutes, the mixture is treated dropwise with absolute ethanol to completely discharge the color. After removal of NH₃, the residue is cooled and treated with water. Further extraction with ether and removal of organic solvent leaves crude 6-amino-1,4,6,7,8,9-hexahydro-5H-benzocycloheptene which is converted to its N-benzoyl derivative with benzoyl chloride-pyridine and thence to the tetrol as described previously.

EXAMPLE 44

A mixture of 16.0 g. (0.1 mole) of 5, 6, 8, 9-tetrahydro-7H-cycloheptabenzen-7-one and 42.4 g. (0.1 mole) of cyanobutyltriphenylphosphonium bromide in 500 ml of dimethoxyethane is stirred under nitrogen and treated portion-wise with 0.11 mole of 50% NaH dispersed in mineral oil. After several hours, the mixture is freed of solvent and the product extracted into ether. The crude product is dissolved in ethanol, treated with $NH_3$ and 10 g. of Raney nickel and hydrogenated at 1500 psi of hydrogen at 100°–120°. After uptake is complete, the mixture is cooled, freed of catalyst and the product isolated from solvent. The crude 7-aminopentyl-6, 7, 8, 9-tetrahydro-5H-benzocycloheptene is taken up in 100 ml of ether and added to 500 ml of liq. $NH_3$. The solution is treated with 20 g of lithium in small pieces over 1 hour. Then absolute ethanol is added slowly dropwise to discharge the color. After removal of $NH_3$, the mixture is cooled, treated with water, and extracted with ether. Removal of solvents leaves crude 7-aminopentyl-1,4,6,7,8,9-hexahydro-5H-benzocycloheptene which is converted to its N-benzoyl derivative and thence to the tetrol as described previously.

What is claimed is:

1. A compound of the structure

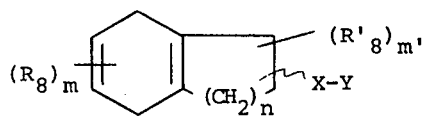

wherein X is a single bond or a straight or branched chain alkylene radical having from one to about 10 carbon atoms, Y is

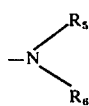

wherein $R_5$ and $R_6$ are the same or different and are selected from the group consisting of hydrogen, lower alkyl, lower alkoxyalkyl, halo-lower alkyl, monocyclic cycloalkyl having 3 to 6 ring members, monocyclic cycloalkyl lower alkyl, wherein the cycloalkyl has 3 to 6 ring members, lower alkanoyl, halo-lower alkanoyl, hydroxy-lower alkyl, phenyl, lower alkylphenyl, di(-lower alkyl)phenyl, halophenyl, mono-, di- or trinitrophenyl, phenylalkyl, benzoyl, monocyclic heterocyclic, monocyclic heterocyclicalkyl or N,N-dialkylsulfamoyl; wherein alkyl contains 1 to 8 carbons, and

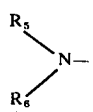

can be taken together to form a heterocyclic radical; wherein the heterocyclic radicals repesented by $R_5$, $R_6$ or

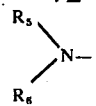

taken together contain 5-, 6- or 7-members having less than 21 atoms (excluding hydrogen) and are selected from the group consisting of pyrrolidine, piperidine, morpholine, thiamorpholine, piperazine or homopiperazine, $R_8$ and $R'_8$ are lower alkyl or cycloalkyl having 3 to 6 ring members; and $n$ is 1 to 3; $m$ and $m'$ are 0, 1 or 2; stereoisomers thereof, acid salts thereof, quaternary salts thereof and N-oxides thereof.

2. The compound as defined in claim 1 wherein $R_5$ and $R_6$ are hydrogen.

3. The compound as defined in claim 1 having the structure

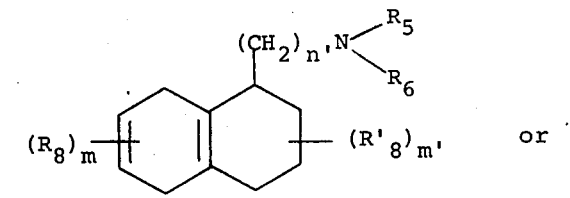

or

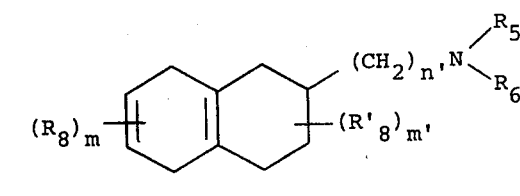

wherein $n'$ is 0 to 10.

4. The compound as defined in claim 1 having the structure

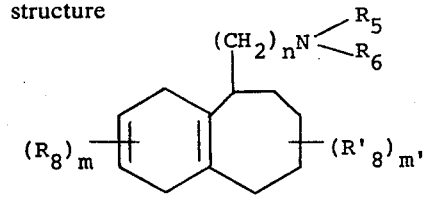

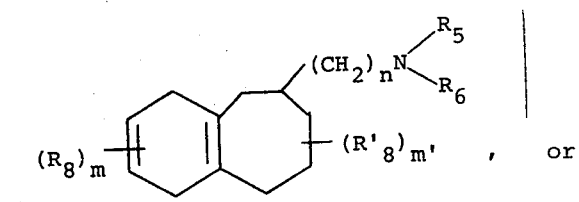

or

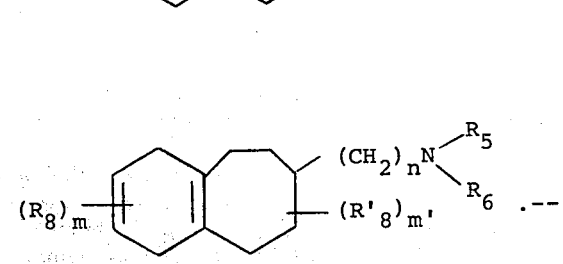

5. The compound as defined in claim 1 having the name 1-[3-(4,7-dihydro-1-indaynl)propyl]piperidine.

6. The compound as defined in claim 1 having the name 1-[3-(4,7-dihydro-1-indanyl)propyl]morpholine.

7. The compound as defined in claim 1 having the name 1-(4,7-dihydro-2-indanyl)piperidine.

8. The compound as defined in claim 1 having the name 1-[3(4,7-dihydro-1-indanyl)propyl]pyrrolidine.

9. The compound as defined in claim 1 having the name 1-[2-(4,7-dihydro-2-indanyl)ethyl]piperidine.

10. The compound as defined in claim 1 having the name 4,7-dihydro-N,N-dimethyl-1-indanpropylamine.

11. The compound as defined in claim 1 having the name 4,7-dihydro-indanpropylamine.

12. The compound as defined in claim 1 having the name 4,7-dihydro-1-indanyl piperidine.

13. The compound as defined in claim 1 having the name 1,2,3,4,5,8-hexaydro-1-diethylaminopropylnaphthalene.

14. The compound as defined in claim 1 having the name 6-amino-1,4,6,7,8,9-hexahydro-5H-benzocycloheptene.

15. The compound as defined in claim 1 having the name 7-aminopentyl-1,4,6,7,8,9-hexahydro-5H-benzocycloheptene.

* * * * *

UNITED STATES PATENT AND TRADEMARK OFFICE
CERTIFICATE OF CORRECTION

PATENT NO. : 3,984,407
DATED : October 5, 1976
INVENTOR(S) : Frederic Peter Hauck et al.

It is certified that error appears in the above-identified patent and that said Letters Patent are hereby corrected as shown below:

Column 2, line 6, "N,-N-" should read --N,N- --.
Column 4, line 66, delete "5,6,7" and insert --fumarate,--.
Column 22, line 5, "rage" should read --range--.
Column 22, line 15, "agent-tetrol" should read --agent:tetrol--.
Column 22, line 40, "agent-tetrol" should read --agent:tetrol--.
Column 23, line 11, "carbonate-tetrol" should read --carbonate:tetrol--.
Column 26, line 9, "a" should read --an--.
Column 27, line 19, after "dilute" insert --base--.
Column 33, line 30, "know" should read --known--.
Column 33, line 40, "Wittic" should read --Wittig--.
Column 33, line 45, "alter-" should read --Alter- --.
Column 34, line 36, "know" should read --known--.
Column 39, formula 15 should read

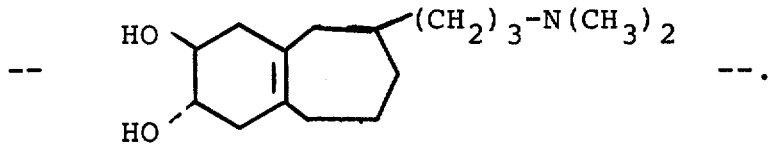

Column 43, Table A, the beginning of line g) should read --n'=7,--
Column 43, Table B, under column headed $R_6$, lines a) and e) should read --H--.
Column 45, Table D, under column headed $R_7$, line e) should read --H--.
Column 47, line 60 should read --1-[5-(Inden-3-yl)pentyl]-pyridinium bromide--.
Column 48, line 18, "5,6trans" should read --5,6-trans--.
Column 50, line 12, "(0068M)" should read --(0.068M)--.
Column 50, line 31, "aount" should read --amount--.
Column 50, line 37, "c,60.93" should read --C, 60.93--.

UNITED STATES PATENT AND TRADEMARK OFFICE
CERTIFICATE OF CORRECTION

PATENT NO. : 3,984,407

DATED : October 5, 1976

INVENTOR(S) : Frederic Peter Hauck et al.

It is certified that error appears in the above-identified patent and that said Letters Patent are hereby corrected as shown below:

Column 50, line 45, "67a" should read --6,7a--.
Column 52, line 17, "hating" should read --heating--.
Column 54, line 25, after "1-[3-" insert --(3- --.
Column 56, line 24, after "1-[2-" insert --(2- --.
Column 59, line 64, "50°" should read --55°--.
Column 66, line 7, "int" should read --into--.
Column 73, line 2, "indaynl" should read --indanyl--.
Column 73, line 8, "3(4,7" should read --3-(4,7--.

Signed and Sealed this

Nineteenth Day of April 1977

[SEAL]

Attest:

RUTH C. MASON
Attesting Officer

C. MARSHALL DANN
Commissioner of Patents and Trademarks